(12) United States Patent
Masubuchi et al.

(10) Patent No.: US 12,178,466 B2
(45) Date of Patent: *Dec. 31, 2024

(54) MEDICAL DEVICE AND TREATMENT METHOD FOR CRUSHING OBJECT IN BODY LUMEN

(71) Applicant: TERUMO KABUSHIKI KAISHA, Tokyo (JP)

(72) Inventors: Yuki Masubuchi, Cupertino, CA (US); Masaomi Imai, Kofu (JP); Takashi Kitaoka, San Jose, CA (US); Takahiro Chida, Cupertino, CA (US); Kazuaki Kanamoto, Hadano (JP); Yukitoshi Kato, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 380 days.

This patent is subject to a terminal disclaimer.

(21) Appl. No.: 17/680,025

(22) Filed: Feb. 24, 2022

(65) Prior Publication Data

US 2022/0233212 A1    Jul. 28, 2022

Related U.S. Application Data

(63) Continuation of application No. 16/124,681, filed on Sep. 7, 2018, now Pat. No. 11,291,467, and a (Continued)

(30) Foreign Application Priority Data

Mar. 9, 2016    (JP) .................................. 2016-045553

(51) Int. Cl.
*A61B 17/221*    (2006.01)
*A61B 17/3207*    (2006.01)
(Continued)

(52) U.S. Cl.
CPC .... *A61B 17/320725* (2013.01); *A61B 17/221* (2013.01); *A61B 17/3207* (2013.01); (Continued)

(58) Field of Classification Search
CPC .......... A61B 17/320725; A61B 17/221; A61B 17/3207; A61B 17/320758; (Continued)

(56) References Cited

U.S. PATENT DOCUMENTS 5,376,100 A    12/1994    Lefebvre
5,766,191 A    6/1998    Trerotola
(Continued)

FOREIGN PATENT DOCUMENTS

JP    5329166 A    12/1993
JP    2004500171 A    1/2004
(Continued)

OTHER PUBLICATIONS

International Search Report (PCT/ISA/210) mailed on Apr. 11, 2017, by the Japanese Patent Office as the International Searching Authority for International Application No. PCT/JP2017/009016.
(Continued)

*Primary Examiner* — Mohamed G Gabr
*Assistant Examiner* — Aman Kumar Mann
(74) *Attorney, Agent, or Firm* — BUCHANAN INGERSOLL & ROONEY PC

(57) ABSTRACT

A medical device for crushing an object in a body lumen, the medical device including: an elongated shaft portion rotatably driven; a crushing unit provided with bendable wire rods and rotatable together with the shaft portion; and a sliding unit fixed to each of end portion of the wire rods on at least one of a distal side of and a proximal side of the wire rods and is interlocked with the shaft portion so as to be slidable in an axial direction of the shaft portion. The shaft
(Continued)

portion is provided with contact portions that come into contact with the sliding unit during rotation and limit relative rotation of the shaft portion and the sliding unit. After the sliding unit is attached to the contact portions, the sliding unit rotates in the same direction as the shaft portion along with the rotation of the shaft portion.

15 Claims, 16 Drawing Sheets

Related U.S. Application Data continuation of application No. PCT/JP2017/009016, filed on Mar. 7, 2017.

(51) Int. Cl.
*A61F 2/01* (2006.01)
*A61B 17/22* (2006.01)

(52) U.S. Cl.
CPC .............. *A61B 17/320758* (2013.01); *A61B 17/320783* (2013.01); *A61F 2/013* (2013.01); *A61B 2017/22039* (2013.01); *A61B 2017/2212* (2013.01); *A61B 2017/320716* (2013.01); *A61B 2017/320733* (2013.01); *A61B 2017/320775* (2013.01)

(58) Field of Classification Search
CPC .. A61B 17/320783; A61B 2017/22039; A61B 2017/2212; A61B 2017/320716; A61B 2017/320733; A61B 2017/320775; A61B 17/320016; A61B 2017/320008; A61B 2017/320064; A61B 2217/007; A61B 17/22; A61B 17/32056; A61B 17/32037; A61F 2/013; A61F 2002/018; A61F 2002/016
See application file for complete search history.

(56) References Cited

U.S. PATENT DOCUMENTS

| | | | |
|---|---|---|---|
| 5,795,322 A | | 8/1998 | Boudewijn |
| 5,836,868 A | * | 11/1998 | Ressemann .... A61B 17/320725 606/159 |
| 5,895,402 A | | 4/1999 | Hundertmark et al. |
| 6,371,971 B1 | | 4/2002 | Tsugita et al. |
| 6,702,830 B1 | * | 3/2004 | Demarais .............. A61M 29/02 606/159 |
| 8,454,057 B2 | * | 6/2013 | Gipson ............... F16L 13/0245 285/294.1 |
| 2004/0082962 A1 | | 4/2004 | Demarais et al. |
| 2007/0005093 A1 | * | 1/2007 | Cox ....................... A61B 90/30 606/198 |
| 2008/0255596 A1 | | 10/2008 | Jenson et al. |
| 2009/0099583 A1 | | 4/2009 | Butterfield et al. |
| 2010/0121361 A1 | | 5/2010 | Plowe et al. |
| 2010/0137892 A1 | | 6/2010 | Dreher et al. |
| 2013/0060270 A1 | | 3/2013 | Teeslink et al. |
| 2016/0374714 A1 | * | 12/2016 | Majercak ....... A61B 17/320725 606/159 |
| 2017/0238960 A1 | | 8/2017 | Hatta et al. |
| 2019/0000500 A1 | | 1/2019 | Masubuchi et al. |

FOREIGN PATENT DOCUMENTS

| | | |
|---|---|---|
| JP | 2013521897 A | 6/2013 |
| JP | 2014039851 A | 3/2014 |
| JP | 5800439 B2 | 10/2015 |
| WO | 9424946 A1 | 11/1994 |
| WO | 2014141226 A1 | 9/2014 |
| WO | 2015190578 A1 | 12/2015 |

OTHER PUBLICATIONS

Written Opinion (PCT/ISA/237) mailed on Apr. 11, 2017, by the Japanese Patent Office as the International Searching Authority for International Application No. PCT/JP2017/009016.
The extended European Search Report issued on Sep. 4, 2019, by the European Patent Office in corresponding European Patent Application No. 17763249.4-1113. (8 pages).

* cited by examiner

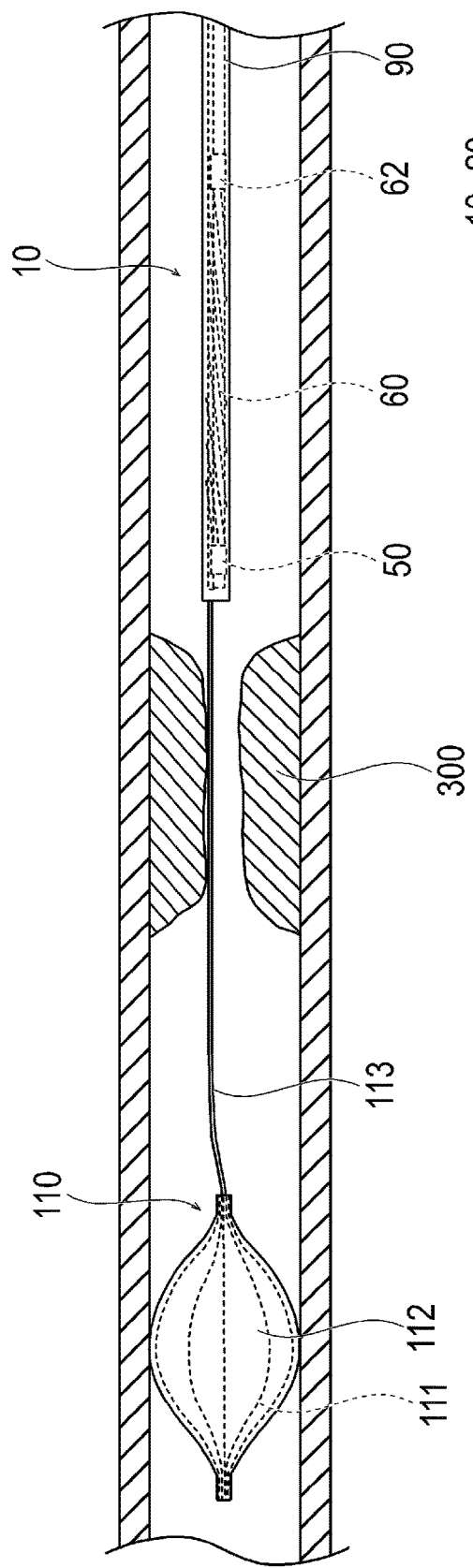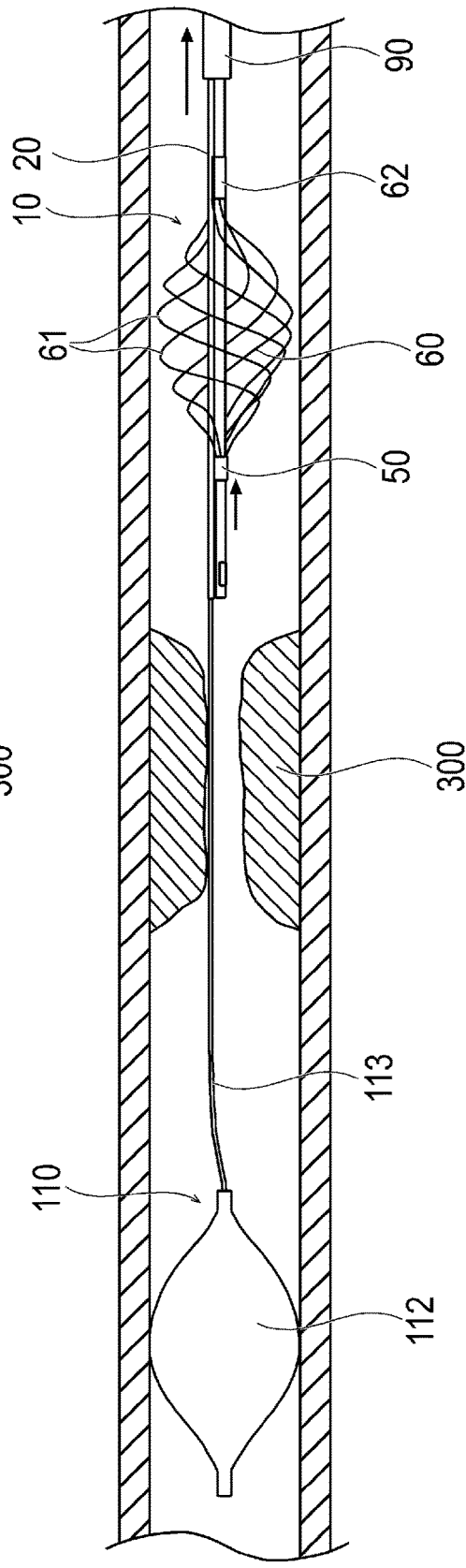

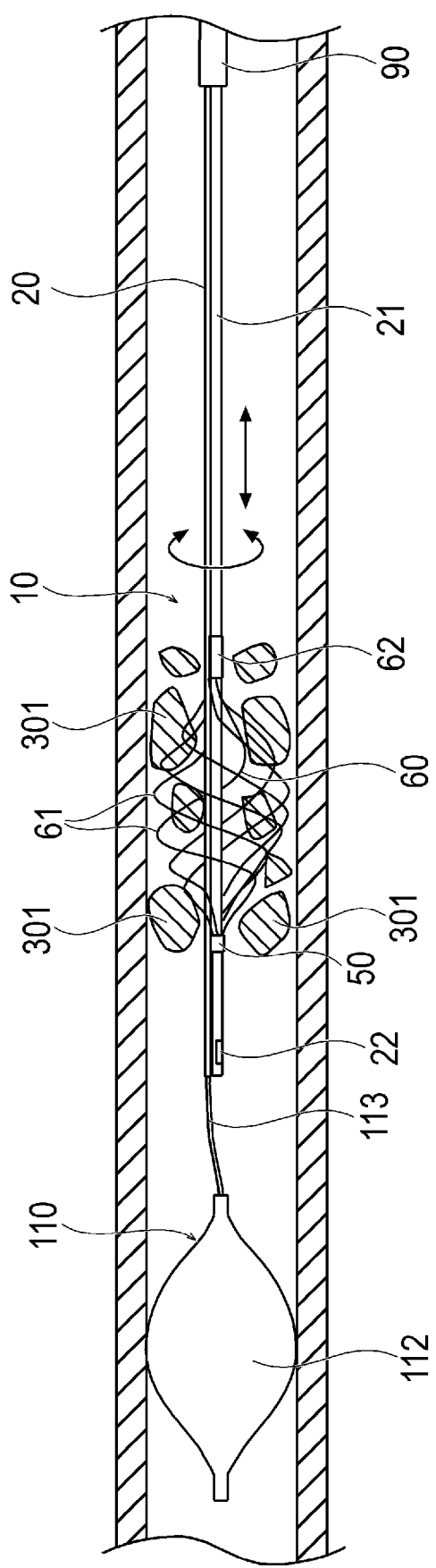

FIG.15 (A)
FIG. 15(B)
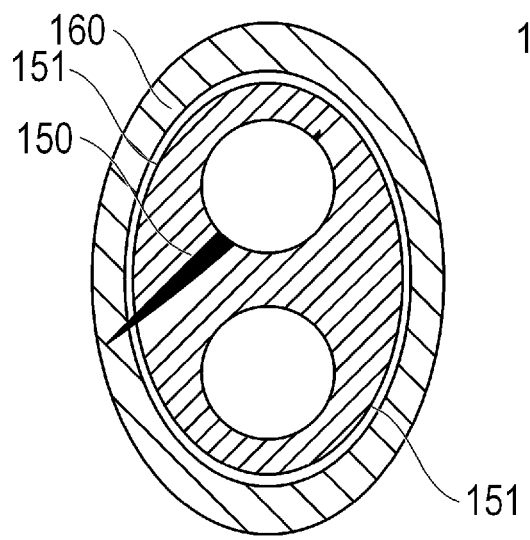
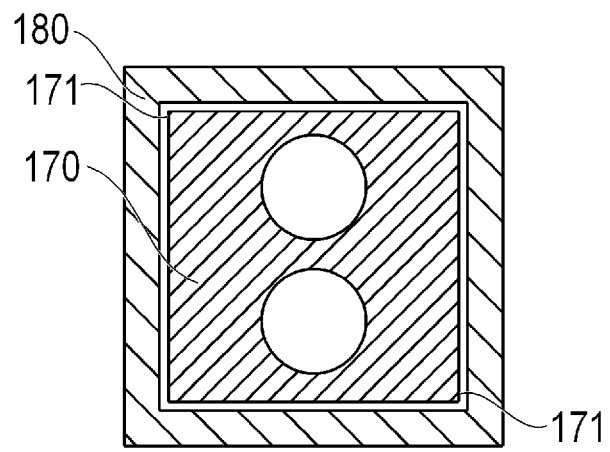
FIG.16
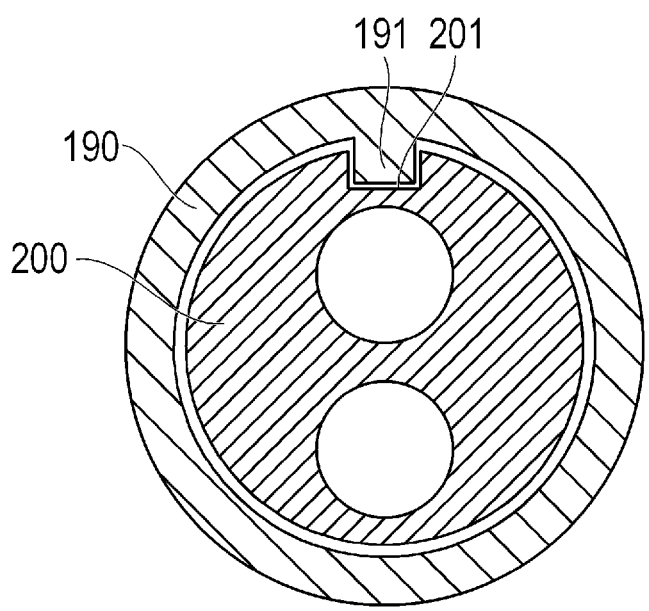

MEDICAL DEVICE AND TREATMENT METHOD FOR CRUSHING OBJECT IN BODY LUMEN

CROSS-REFERENCE TO RELATED APPLICATIONS

This application is a continuation of U.S. application Ser. No. 16/124,681 filed Sep. 7, 2018, which is a continuation of International Application No. PCT/JP2017/009016 filed on Mar. 7, 2017, and claims priority to Japanese Application No. 2016-045553 filed on Mar. 9, 2016, the entire content of each of which is incorporated by reference herein.

TECHNICAL FIELD

The present invention relates to a medical device and a treatment method using the medical device for crushing an object in a body lumen.

BACKGROUND ART

In a case where a thrombus occurs in a body lumen, it is necessary to promptly remove the thrombus. An example of a thrombus that occurs in the body lumen includes a deep vein thrombosis due to a thrombus in a vein in a deep portion of a body, such as a femoral vein or a popliteal vein. As a medical treatment method for the deep vein thrombosis, a method has been known for removing a thrombus by inserting an elongated tubular body of a medical device into a blood vessel, injecting a medicine such as a thrombolytic agent in an embolus, and dissolving the thrombus.

Since a medical treatment method of injecting a medicine for removing a thrombus entails a side effect such as bleeding, there is proposed a medical treatment method in which a member of a wire rod is provided at a distal portion of a shaft inserted into a blood vessel is rotated, and thereby the thrombus that comes into contact with the member is mechanically broken and removed (for example, refer to U.S. Pat. No. 5,766,191). Consequently, it is not necessary to inject a medicine or it is possible to reduce the medicine usage.

The member that mechanically breaks the thrombus is a bent wire rod. It is preferable that the wire rod is able to be deformed into a linear shape in order to reach a target position. Hence, a first end portion of the wire rod is fixed to a shaft portion, but a second end portion of the wire rod is not fixed to the shaft portion. Therefore, when the shaft portion is rotated, the wire rod comes into contact with the thrombus, thereby receiving a reaction force, and is twisted and deformed. Thus, the range in which the wire rod is able to break the thrombus continually changes.

SUMMARY OF INVENTION

The disclosure herein provides a medical device and a treatment method using the medical device by which it is possible to appropriately maintain a range in which it is possible to break an object formed in a body lumen.

According to the disclosure, there is provided a medical device for crushing an object in a body lumen by being inserted into the corresponding body lumen, the medical device including: an elongated shaft portion that is rotatably driven; a crushing unit provided with bendable wire rods and is rotatable together with the shaft portion; and a sliding unit that is fixed to each of end portion of the wire rods on at least one of a distal side and a proximal side thereof and is interlocked with the shaft portion so as to be slidable in an axial direction of the shaft portion. The shaft portion is provided with a contact portion that comes into contact with the sliding unit during rotation and limits the relative rotation of the shaft portion and the sliding unit. After the sliding unit is attached to the contact portion, the sliding unit rotates in the same direction as the shaft portion along with the rotation of the shaft portion.

According to the another aspect of the disclosure, there is provided a treatment method for crushing an object formed in a lesion area in a body lumen by using the medical device described above, the treatment method including: inserting the shaft portion into the body lumen and delivering the crushing unit to the lesion area; rotating the shaft portion and causing the sliding unit to be attached to the contact portion of the shaft portion; and simultaneously rotating an end portion of the crushing unit on a distal side and an end portion of the crushing unit on a proximal side by the shaft portion, causing the crushing unit to come into contact with the object, and crushing the g object.

In the medical device and the treatment method configured as described above, the shaft portion rotates, and thereby the contact portion of the shaft portion comes into contact with the sliding unit such that the relative rotation of the shaft portion and the sliding unit is limited. Consequently, the crushing unit is unlikely to be twisted even when receiving an external force in a rotating direction and is unlikely to be deformed, and thus it is possible to appropriately maintain a range in which the crushing unit can crush the object in the body lumen.

BRIEF DESCRIPTION OF THE DRAWINGS

FIG. 7(A) shows a state in which the medical device is inserted into the blood vessel, and FIG. 7(B) shows a state in which a crushing unit of the medical device is exposed in the blood vessel.

FIG. 8 is a longitudinal-sectional view showing a state in which a thrombus is crushed by the medical device.

FIG. 15(A) shows a third modification example in which each of the shaft portion and the sliding unit has an elliptic cross-sectional shape, and 15(B) shows a fourth modification example in which each of the shaft portion and the sliding unit has a quadrangular cross-sectional shape.

FIG. 16 is a cross-sectional view showing a fifth modification example of the medical device.

DESCRIPTION OF EMBODIMENTS

Figure 1:
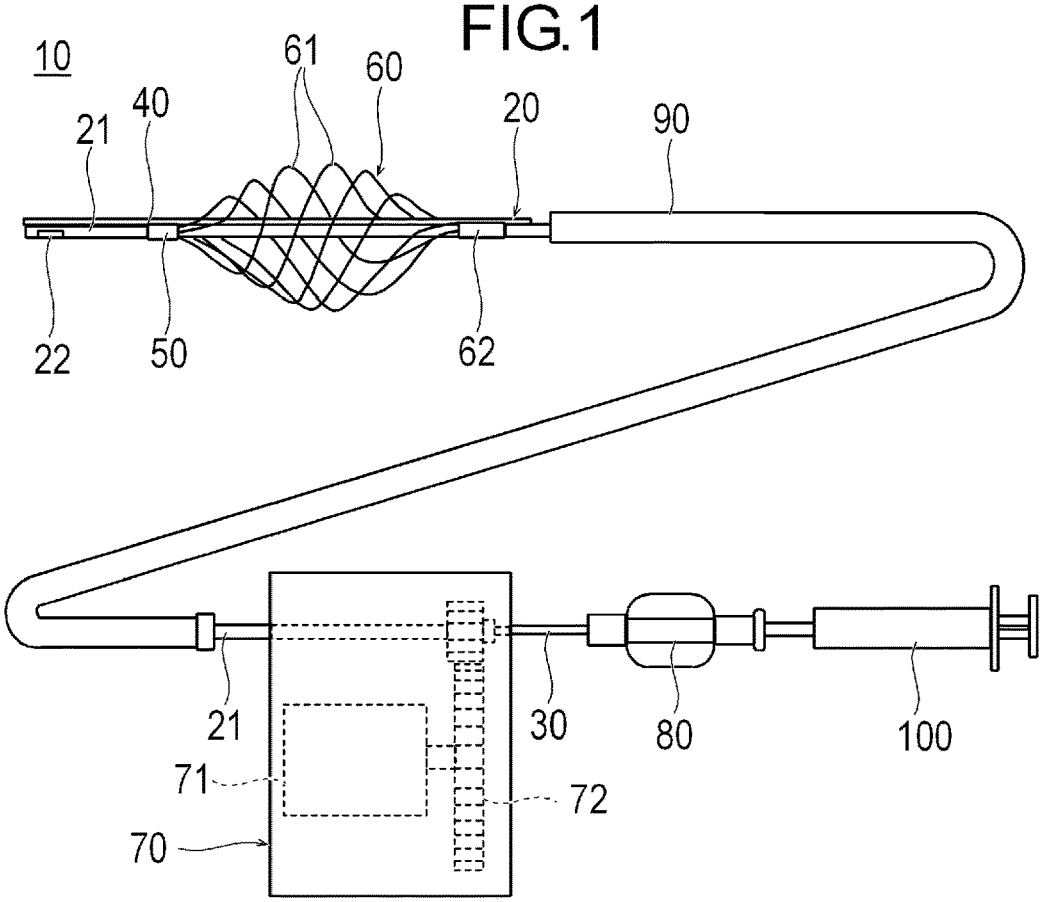
FIG. 1 is a plan view showing a medical device according to an exemplary embodiment.

Hereinafter, an exemplary embodiment of the disclosure will be described with reference to the figures. A medical device 10 according to the exemplary embodiment is inserted into a blood vessel and is used for a treatment of crushing and removing a thrombus in a deep-vein thrombosis. In this specification, a side of the device, on which the device is inserted into a blood vessel, is referred to as a "distal side", and a hand side, on which an operation is performed, is referred to as a "proximal side". Note that an object to be removed is not absolutely limited to the thrombus but can correspond to any object that can be present in a body lumen. Note that a dimensional ratio in the figures is enlarged depending on the description and the ratio is different from an actual ratio in some cases.

As shown in FIGS. 1 to 4, the medical device 10 includes a shaft portion 20 that is elongated and is configured to be rotatably driven, an outer sheath 90 that is able to accommodate the shaft portion 20, a sliding unit 50 that is capable of sliding with respect to the shaft portion 20, and a crushing unit 60 that is configured to be rotated by the shaft portion 20. The medical device 10 further includes a rotation-drive unit 70 that rotates the shaft portion 20, a hub 80 that is provided at a proximal end portion of the shaft portion 20, and a syringe 100 that is connected to a proximal side of the hub 80.

The shaft portion 20 includes a shaft outer tube 21 (first tubular body), a shaft inner tube 30, and a tubular body 40 (a second tubular body) for a guide wire, each of which has an elongated hollow shape.

The shaft outer tube 21 has a distal end portion that is a distal portion of the shaft portion 20 and a proximal end portion that is positioned in the rotation-drive unit 70. The shaft outer tube 21 is capable of reciprocating rotation in a circumferential direction by the rotation-drive unit 70, i.e., clockwise and counter-clockwise. However, the shaft outer tube 21 is not limited to reciprocating and may rotate in one direction. The shaft outer tube 21 is provided with a lumen 24 (first lumen) that accommodates the shaft inner tube 30 therein. An inner diameter of the shaft outer tube 21 is larger than an outer diameter of the shaft inner tube 30. The shaft outer tube 21 is provided with an opening portion 22 having an elongated shaped hole in an axial direction in the vicinity of the distal portion such that an inside and an outside of the shaft outer tube 21 communicate with each other. The distal end portion of the shaft outer tube 21 is provided with a cylindrical attachment portion 23 that blocks the lumen 24. A proximal surface of the attachment portion 23 is an attachment surface 23A that is opposite to a distal surface of the shaft inner tube 30. The attachment surface 23A is positioned to be closer to a distal side than the distal end portion of the opening portion 22 of the shaft outer tube 21. The attachment portion 23 is formed by stainless steel or the like in the exemplary embodiment.

The shaft inner tube 30 is coaxially housed in a hollow lumen of the shaft outer tube 21. The shaft inner tube 30 is provided with an aspiration lumen 32 which is in a negative pressure state such that an aspiration force is generated. The shaft inner tube 30 is capable of moving with respect to the shaft outer tube 21 in the axial direction. A distal end portion of the shaft inner tube 30 is positioned at a position of a proximal end portion of the opening portion 22 of the shaft outer tube 21 or is positioned to be closer to the proximal side than the proximal end portion of the opening portion 22. A proximal end portion of the shaft inner tube 30 extends to be closer to the proximal side than the proximal end portion of the shaft outer tube 21 and is connected to the hub 80. The syringe 100 is connected to the hub 80, thereby performing aspiration in the aspiration lumen 32 of the shaft inner tube 30, and thus it is possible to cause the aspiration lumen 32 to be in the negative pressure state. A cutting portion 31 is provided in the aspiration lumen 32 in the distal end portion of the shaft inner tube 30. The cutting portion 31 has a sharp blade 31A on the distal side, which is a thin metal plate and has a width corresponding to a diameter of the shaft inner tube 30.

A distal end surface of the blade 31A and a distal end surface of the shaft inner tube 30 are flush, that is, there is no step therebetween. Therefore, when the distal surface of the shaft inner tube 30 is attached to the attachment surface 23A of the attachment portion 23, the blade 31A is also attached to the attachment surface 23A. The shaft inner tube 30 is capable of reciprocating in the axial direction at least from a position of the shaft outer tube 21 closer to a proximal side (a position shown in FIG. 4) than a proximal end of the opening portion 22 to a position at which the shaft inner tube is attached to the attachment surface 23A of the attachment portion 23. The cutting portion 31 is disposed to divide a cross-sectional shape of a hollow portion of the shaft inner tube 30 into two portions.

The tubular body 40 for guide wire is disposed to be fixed to the shaft outer tube 21 along an outer surface of a distal portion of the shaft outer tube 21. The tubular body 40 for guide wire is provided with a guide wire lumen 41 (second lumen) into which a guide wire is insertable.

It is preferable that the shaft outer tube 21 is flexible and can transmit acting power of rotation from the proximal side to the distal side. It is preferable that the shaft inner tube 30 is flexible and can transmit acting power of a front and rear reciprocating motion from the proximal side to the distal side. It is preferable that the tubular body 40 for guide wire is flexible. Constituent materials of the shaft outer tube 21, the shaft inner tube 30, and the tubular body 40 for guide wire are not particularly limited; however, it is preferable to use a tubular body having a shape of a multi-layer coil such as a three-layer coil formed in alternate right, left, and right winding directions or a tubular body in which a reinforcing member such as a wire rod is buried, the wire rod being made of a polyolefin such as polyethylene or polypropylene, a polyamide, a polyester such as polyethylene terephthalate, a fluoropolymer such as ethylene-tetrafluoroethylene copolymer (ETFE), polyether ether ketone (PEEK), polyimide, or a combination thereof, for example.

The outer sheath 90 is able to accommodate the shaft portion 20 and is able to accommodate the crushing unit 60 while reducing a diameter of the crushing unit 60 interlocked with the shaft portion 20. The outer sheath 90 is capable of sliding with respect to the shaft portion 20 in the axial direction.

A constituent material of the outer sheath 90 is not particularly limited, however, examples of the material include, preferably, a polyolefin such as polyethylene or polypropylene, a polyamide, polyester such as polyethylene terephthalate, a fluoropolymer such as ETFE, PEEK, polyimide, or the like. In addition, the outer sheath may be formed by a plurality of materials or may have a reinforcing member such as a wire rod which is buried therein.

The crushing unit 60 is provided at a distal portion of the shaft outer tube 21. The crushing unit 60 is provided with a plurality of spiral units 61. The spiral units 61 are all twisted in the same circumferential direction along the axial direction of the shaft outer tube 21. Each of the proximal end portions of the spiral units 61 is fixed to the shaft outer tube 21 at an interlock portion 62. Each of the distal end portions of the spiral units 61 is fixed to the sliding unit 50 that is slidable with respect to the shaft portion 20. The positions at which the spiral units 61 are fixed to the interlock portion 62 and the sliding unit 50 are different from each other in the circumferential direction. The spiral units 61 are aligned in the circumferential direction at a position at which the central portions of the bent spiral units in the axial direction are separated from the shaft outer tube 21 in a radial direction. Consequently, the entire crushing unit 60 uniformly bulges in the circumferential direction. When the shaft portion 20 rotates, the crushing unit 60 rotates along with the shaft portion. Therefore, it is possible to crush a thrombus in a blood vessel or to agitate the crushed thrombus.

The spiral units 61 constituting the crushing unit 60 are made of a thin metal wire having flexibility. The crushing unit 60 is in a state of being housed inside the outer sheath 90 until the shaft portion 20 is inserted into a target site. When the spiral units 61 are accommodated in the outer sheath 90, the sliding unit 50, with which the distal portions of the spiral units 61 are interlocked, is moved to the distal side along the shaft portion 20. Consequently, the bulge of the spiral units 61 at the central portion thereof in the axial direction is decreased, and the spiral units approach an outer peripheral surface of the shaft outer tube 21. Consequently, the spiral units 61 are reduced in diameter and are accommodated inside the outer sheath 90. After the shaft portion 20 is inserted into the target site of a blood vessel, the outer sheath 90 is caused to slide with respect to the shaft portion 20 to the proximal side, and thereby the crushing unit 60 is exposed outside the outer sheath 90 and is expanded by its own elastic force. Here, the sliding unit 50 moves along the shaft portion 20 to the proximal side. Therefore, it is desirable that the spiral units 61 are made of a shape-memory material. Examples of constituent materials of the spiral units 61 include, preferably, a shape-memory alloy to which a shape-memory effect or superelasticity through heat treatment is imparted, stainless steel, or the like. It is preferable to use a Ni—Ti-based alloy, a Cu—Al—Ni-based alloy, a Cu—Zn—Al-based alloy, a combination thereof, or the like as the shape-memory alloy.

Figure 2:
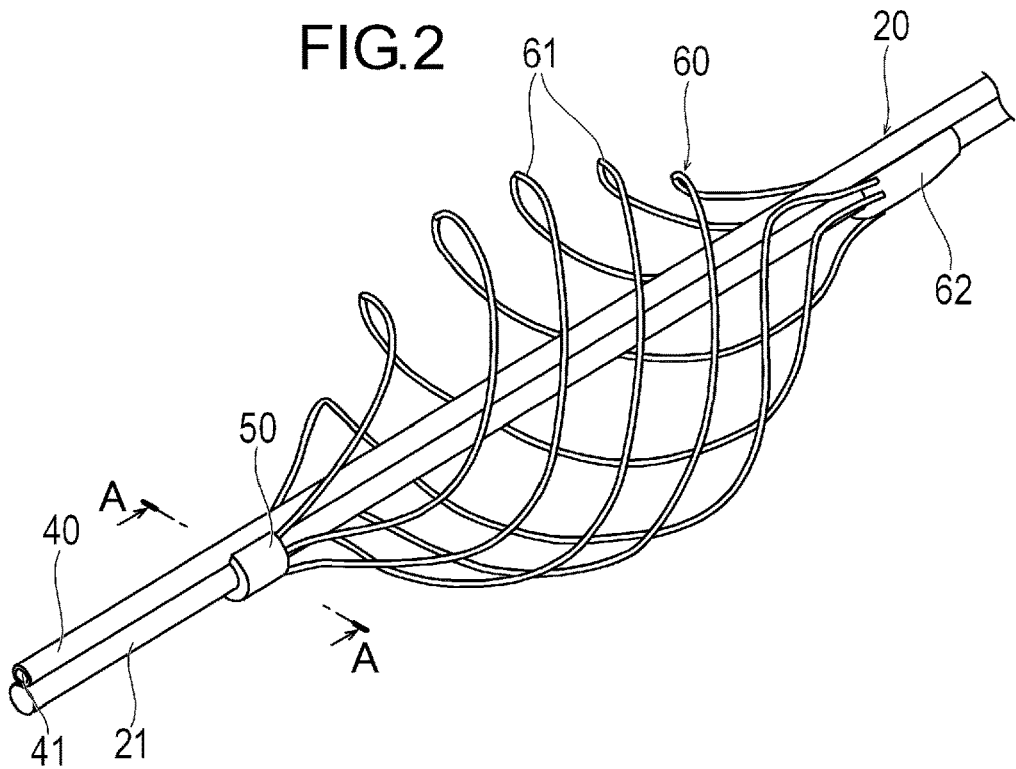
FIG. 2 is a perspective view showing a distal portion of the medical device.
Figure 3:
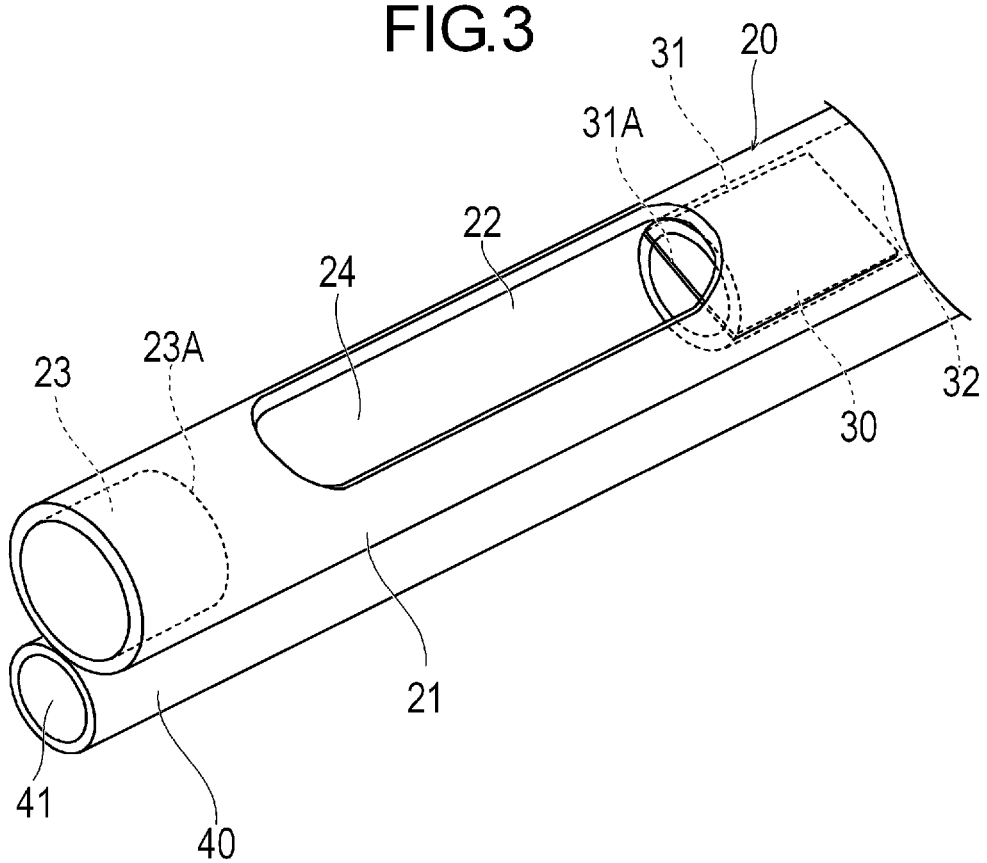
FIG. 3 is an enlarged perspective view showing the distal portion of the medical device.
Figure 4:
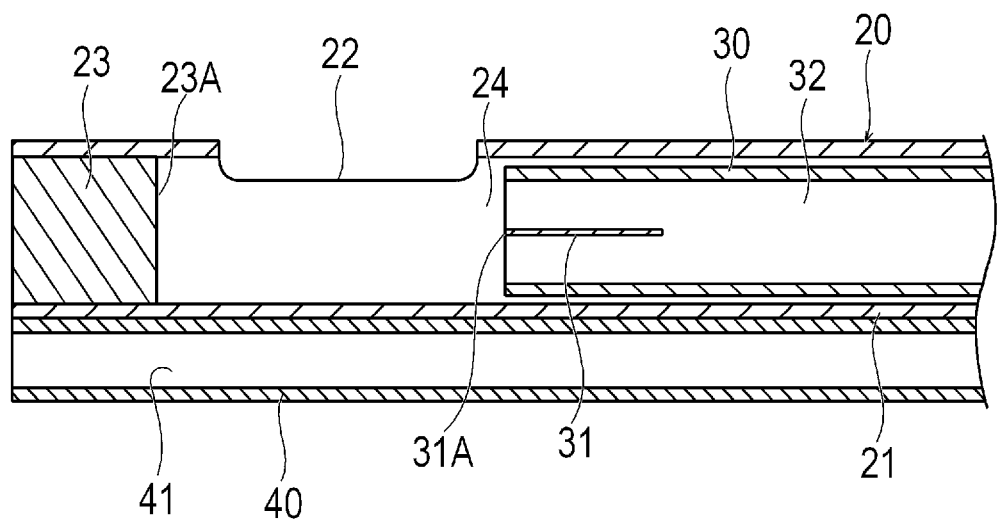
FIG. 4 is a longitudinal-sectional view showing the distal portion of the medical device.
Figure 5:
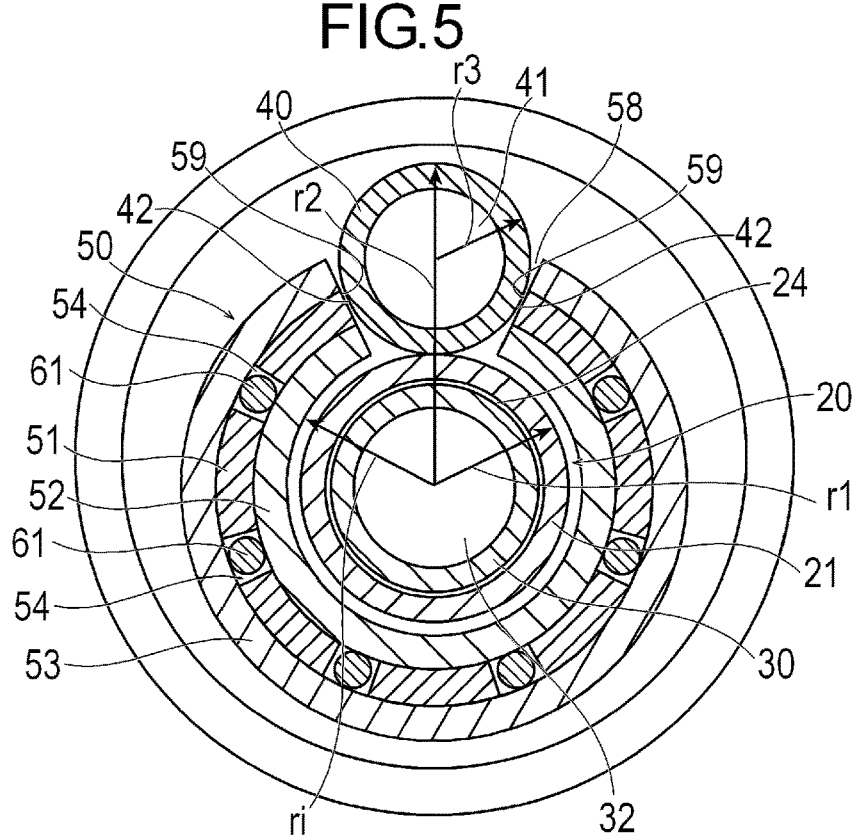
FIG. 5 is a cross-sectional view taken along line A-A in FIG. 2.
Figure 6:
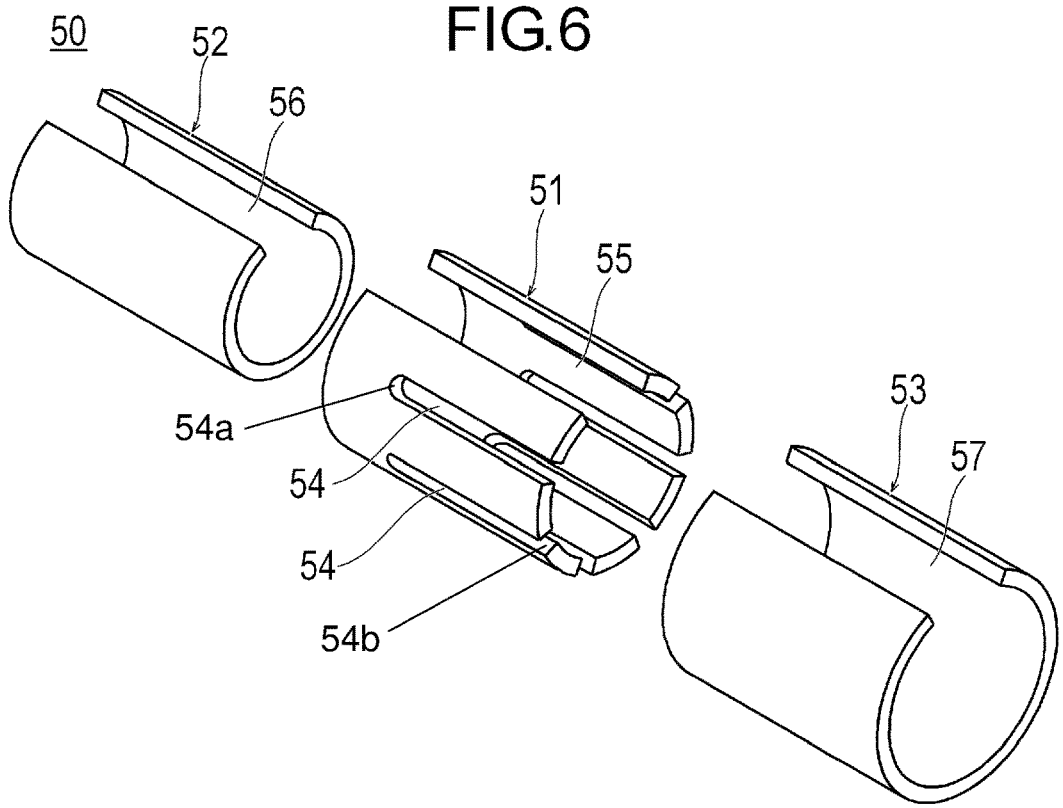
FIG. 6 is an exploded perspective view showing constituent components of a sliding unit according to the exemplary embodiment.

As shown in FIGS. 2, 5, and 6, the sliding unit 50 has a C-shaped cross section that is orthogonal to the axial direction of the shaft portion 20. The sliding unit 50 is provided with a slit 58 that extends from a first end portion to a second end portion of the sliding unit 50 in the axial direction. Note that the "slit" has a different structure from a groove that does not penetrate in that the slit penetrates the sliding unit from a first surface to a second surface in a thickness direction. The sliding unit 50 has a central sliding portion 51 provided with a plurality of accommodation concave portions 54, in which the spiral units 61 are accommodated, an inner sliding portion 52 that is disposed on an inner side of the central sliding portion 51, and an outer sliding portion 53 that is disposed on an outer side of the central sliding portion 51. The central sliding portion 51 is provided with the accommodation concave portions 54, in which the respective spiral units 61 are accommodated, and a first slit 55, in which the tubular body 40 for guide wire is accommodated.

The accommodation concave portions 54 of the central sliding portion 51 have an end portion 54a at a position separated by a predetermined length apart from the proximal side in a central axis direction. Each of distal ends of the spiral units 61 is brought into contact with the end portions 54a of the plurality of accommodation concave portions 54, and thereby the crushing unit 60 can have a uniform diameter. In addition, the positions of the end portions 54a of the plurality of accommodation concave portions 54 can be each changed. Specifically, it is possible to change the predetermined length from the opening portions 54b of the plurality of accommodation concave portions 54 on the proximal side to the end portions 54a thereof on the distal side. The predetermined length from the opening portions 54b of the plurality of accommodation concave portions 54 on the proximal side to the end portions 54a thereof on the distal side can be gradually increased in an arranged order in the circumferential direction. Alternatively, it is possible to alternately change the predetermined length from the opening portions 54b of the plurality of accommodation concave portions 54 on the proximal side to the end portions 54a thereof on the distal side, thus providing the crushing unit 60 with two different diameter possibilities (even though spiral units 61 are all the same size) and two different crushing powers. In addition, the accommodation concave portions, in which the respective spiral units 61 are accommodated, may penetrate from the proximal side to the distal side in the central axis direction. In addition, the accommodation concave portions 54 are aligned in the circumferential direction of the central sliding portion 51. The accommodation concave portion 54 has a size to the extent that the spiral unit 61 can be accommodated therein. The first slit 55 penetrates the central sliding portion 51 from the proximal side to the distal side in the axial direction.

The inner sliding portion 52 is disposed on the inner side of the central sliding portion 51, and an outer peripheral surface of the inner sliding portion 52 is in contact with an inner peripheral surface of the central sliding portion 51. The inner sliding portion 52 is provided with a second slit 56 in which the tubular body 40 for guide wire is accommodated. The second slit 56 penetrates the inner sliding portion 52 from the proximal side to the distal side in the axial direction. An inner peripheral surface of the inner sliding portion 52 slidably is in contact with the outer peripheral surface of the shaft outer tube 21. A clearance between the inner peripheral surface of the inner sliding portion 52 and the outer peripheral surface of the shaft outer tube 21 is 0.02 mm to 0.1 mm, for example.

The outer sliding portion 53 is disposed on the outer side of the central sliding portion 51, and an inner peripheral surface of the outer sliding portion 53 is in contact with an outer peripheral surface of the central sliding portion 51. The outer sliding portion 53 is provided with a third slit 57 in which the tubular body 40 for guide wire is accommodated. The third slit 57 penetrates the outer sliding portion 53 from the proximal side to the distal side in the axial direction.

The central sliding portion 51, the inner sliding portion 52, and the outer sliding portion 53 are fixed by an adhesive or the like in a state in which the first slit 55, the second slit 56, and the third slit 57 are coincident (aligned) with each other, and the distal end portions of the spiral units 61 are inserted into the respective accommodation concave portions 54. The first slit 55, the second slit 56, and the third slit 57 configure one slit 58. The inner peripheral surface of the inner sliding portion 52 slidably comes into contact with the outer peripheral surface of the shaft outer tube 21. The tubular body 40 (convex portion) for guide wire is accommodated in the slit 58 of the sliding unit 50. Consequently, the distal portions of the spiral units 61 are fixed to the sliding unit 50 and the sliding unit 50 is slidable on the outer peripheral surface of the shaft outer tube 21. When the shaft portion 20 rotates, a contact portion 42, which is a part of an outer peripheral surface of the tubular body 40 for guide wire, comes into contact with an end surface 59 that forms an edge portion of the slit 58. Consequently, relative rotation of the sliding unit 50 and the shaft portion 20 is limited. A relative rotary angle between the sliding unit 50 and the shaft portion 20 is preferably 180 degrees or smaller, more preferably 90 degrees or smaller, still more preferably 4 degrees or smaller. Hence, it is preferable that a clearance between the end surface 59 of the slit 58 and the contact portion 42 of the tubular body 40 for guide wire is set to be equal to the relative rotary angle.

When r1 represents a radius from the center of the shaft outer tube 21, which is the rotation center, to the closest outer peripheral surface (outer peripheral surface of the shaft outer tube 21) of the shaft portion 20, r2 represents a radius from the center described above to the remotest outer peripheral surface (outer peripheral surface of the tubular body 40 for guide wire) of the shaft portion 20, and ri represents a radius to an inner peripheral surface of the sliding unit 50, which has the smallest radius, Expression (1) set forth below is satisfied. Consequently, the rotation of the shaft portion 20 causes the shaft portion 20 to reliably come into contact with the sliding unit 50, and thus the relative rotation of the sliding unit 50 and the shaft portion 20 is limited.

$$r1 < ri < r2 \qquad \text{Expression (1)}$$

In addition, the radius r1 of the shaft outer tube 21 to the outer peripheral surface thereof is larger than a radius r3 of the tubular body 40 for guide wire to the outer peripheral surface thereof. Consequently, it is possible to effectively use the tubular body 40 for guide wire, which has a smaller radius than that of the shaft outer tube 21, as a convex portion that is fitted into the slit 58. In addition, an outer diameter of the shaft outer tube 21 is larger than a width between opposite end surfaces 59 of the edges of the slit 58. Consequently, it is possible to suppress deviation of the shaft outer tube 21 from the slit 58. In addition, an outer diameter of the tubular body 40 for guide wire is smaller than a width of the slit 58. Consequently, the tubular body 40 for guide wire can be reliably moved inside the slit 58.

Constituent materials of the central sliding portion 51, the inner sliding portion 52, and the outer sliding portion 53 are not particularly limited as long as shapes of the portions are maintained; however, examples of materials include, preferably, stainless steel, aluminum, a polyolefin such as polyethylene or polypropylene, a polyamide, polyester such as polyethylene terephthalate, a fluoropolymer such as ETFE, PEEK, polyimide, or the like. The central sliding portion 51 may be configured of a different material from a material of the inner sliding portion 52 and the outer sliding portion 53. For example, the inner sliding portion 52 can be configured of a fluoropolymer having a low friction coefficient so as to easily slide with respect to the shaft portion 20, the outer sliding portion 53 can be configured of a flexible resin material such that a blood vessel is not damaged, and the central sliding portion 51 can be configured of stainless steel having high stiffness such that it is possible to reliably hold the spiral units 61.

As shown in FIG. 1, the rotation-drive unit 70 includes a drive motor 71 and a gear portion 72 that links the drive motor 71 to the shaft outer tube 21 of the shaft portion 20. The drive motor 71 is rotated, and thereby the shaft outer tube 21 rotates in the circumferential direction. In the exemplary embodiment, the shaft outer tube 21 is driven by the drive motor 71 so as to rotate alternately in a positive direction and a negative direction of the circumferential direction. Alternate rotation in the positive and negative directions enables bloodstream to flow alternately in opposite directions.

Next, a method of using the medical device 10 according to the exemplary embodiment is exemplified in a case where the thrombus in the blood vessel is crushed and aspirated.

Before the shaft portion 20 of the medical device 10 of the exemplary embodiment is inserted, it is desirable that a protective member such as a filter or a balloon that limits circulation of a fluid in the blood vessel is disposed on a downstream side (side to which the bloodstream flows) from the thrombus in the blood vessel. In the embodiment, as shown in FIG. 7(A), a filter device 110 that includes an elastic body 111 made of a wire rod that is expanded by own elastic force by being pushed out from a sheath or the like, a film-shaped filter 112 that is disposed on an outer peripheral surface of the elastic body 111, and a wire portion 113 that is interlocked with the elastic body 111 is used. When the elastic body 111 pushed out from the sheath or the like is expanded, and the filter 112 comes into contact with the blood vessel, the filter 112 limits circulation of blood. Consequently, the crushed thrombus can be prevented from flowing in the blood vessel and moving to another position.

Next, the medical device 10, which is in a state in which the distal portion of the shaft portion 20 including the crushing unit 60 is housed in the outer sheath 90, is prepared. Next, the guide wire lumen 41 (refer to FIG. 4) of the medical device 10 is inserted into a proximal end portion of the wire portion 113. Next, the medical device 10 is caused to reach a proximal side of a thrombus 300 with the wire portion 113 as a guide. Then, when the outer sheath 90 is moved with respect to the shaft portion 20 to the proximal side, the outer sheath 90 is caused to slide with respect to the shaft portion 20 to the proximal side, the crushing unit 60 is exposed outside the outer sheath 90 and is expanded by own elastic force, as shown in FIG. 7(B). Here, the sliding unit 50 moves with respect to the shaft portion 20 to the proximal side.

Next, when the rotation-drive unit 70 (refer to FIG. 1) rotates the shaft outer tube 21 in a state in which the crushing unit 60 approaches the vicinity of the thrombus 300, the crushing unit 60 also rotates along with rotation of the shaft outer tube. In this state, when the medical device 10 is moved to the distal side, the crushing unit 60 is brought into contact with the thrombus 300, and the crushing unit 60 crushes the thrombus 300 that is in a state of being fixed in the blood vessel. When the crushing unit 60 continues to rotate, the filter device 110 limits the flowing of the blood, and the thrombus 300 that is in a state of being fixed to the blood vessel is crushed as shown in FIG. 8. A crushed thrombus 301 (thrombus 300 that has been crushed into pieces) is in a floating state without being settled in the blood vessel in which the thrombus is located.

When the crushing unit 60 is rotated, thereby coming into contact with the thrombus 300, the crushing unit receives a reacting force in an opposite direction to the rotation direction. A proximal portion of the crushing unit 60 is fixed to the shaft portion 20 by the interlock portion 62. In addition, a distal portion of the crushing unit 60 is interlocked with the sliding unit 50, and relative rotation of the sliding unit 50 with respect to the shaft portion 20 is limited. In other words, when the shaft portion 20 rotates, the contact portions 42 of the shaft portion 20 come into contact with the end surfaces 59 of the slit 58 of the sliding unit 50 (refer to FIG. 5) such that the relative rotation of the sliding unit 50 with respect to the shaft portion 20 is limited. Therefore, relative rotation of the end portion on the proximal side and the end portion on the distal side of the crushing unit 60 is limited, and thus twisting of the crushing unit 60 is suppressed. After the sliding unit 50 comes into contact with the contact portions 42 of the shaft portion 20, it is possible to rotate a second end portion (end portion on the proximal side) of the crushing unit 60 which is fixed to the shaft portion 20 and a first end portion (end portion on the distal side) of the crushing unit 60 which is fixed to the sliding unit 50, along with rotation of the shaft portion 20. Here, positions of the first end portion and the second end portion of the crushing unit 60 in the circumferential direction are fixed with respect to the shaft portion 20. For example, when the spiral units 61 are twisted in a direction in which spirals of the spiral units 61 are removed (a direction in which the spiral unit has a shape approximating to a straight line without a spiral), a bulge (outer diameter) of the crushing unit 60 increases, and a range, in which it is possible to crush the thrombus, increases. In addition, when the spiral units 61 are twisted in a direction in which the spirals of the spiral units 61 are stronger (an opposite direction to the direction in which the spirals of the spiral units are removed), the bulge (outer diameter) of the crushing unit 60 decreases, and a range, in which it is possible to crush the thrombus, decreases. In particular, in a case where the thrombus is crushed while the rotating direction of the crushing unit 60 is alternately changed in the positive and negative directions, the outer diameter of the crushing unit 60 changes whenever the rotating direction changes, and the range in which it is possible to crush the thrombus changes. In the exemplary embodiment, the crushing unit 60 is unlikely to be twisted, and thereby the size of the bulge of the crushing unit 60 can be maintained. Thus, it is possible to appropriately maintain the range, in which it is possible to crush the thrombus.

When the crushing unit 60 moves forward or retreats in the blood vessel having an inner diameter that changes, an outer diameter of the crushing unit 60 changes along with the inner diameter of the blood vessel. Here, in order to change the outer diameter of the crushing unit 60, the sliding unit 50 moves forward or retreats along the shaft portion 20 in the axial direction. Further, while the outer diameter of the crushing unit 60 changes depending on the movement of the sliding unit 50, the crushing unit rotates in the circumferential direction and crushes the thrombus 300.

Figure 9:
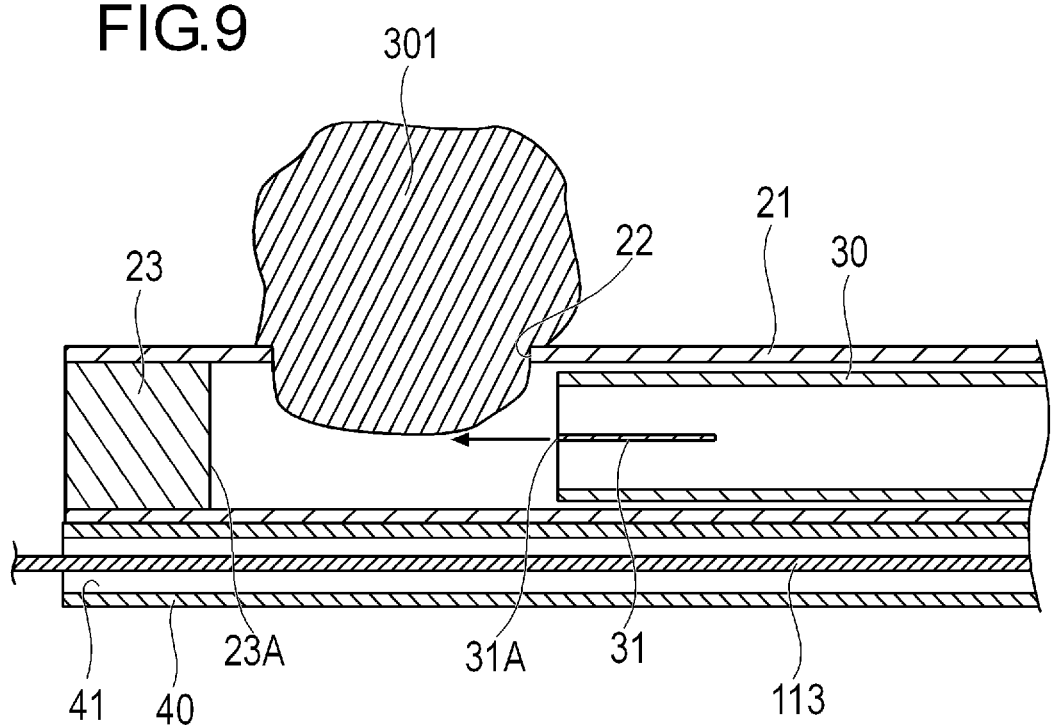
FIG. 9 is an enlarged longitudinal-sectional view of the distal portion of the medical device, which shows a state in which the crushed thrombus is aspirated to an opening portion of a shaft outer tube.

Next, the syringe 100 (refer to FIG. 1) pulls a plunger and causes the aspiration lumen 32 of the shaft inner tube 30 to be in a negative pressure state. Since the distal end portion of the shaft inner tube 30 communicates with the hollow inside of the shaft outer tube 21, and the shaft outer tube 21 communicates with an outer portion of the shaft portion 20 through the opening portion 22, an aspiration force is generated in the opening portion 22 with respect to an outer portion of the shaft portion 20. Therefore, the opening portion 22 attracts the crushed thrombus 301 that floats in the blood vessel. As shown in FIG. 9, a part of the thrombus 301 attracted to the opening portion 22 infiltrates into the hollow inside of the shaft outer tube 21.

Figure 10:
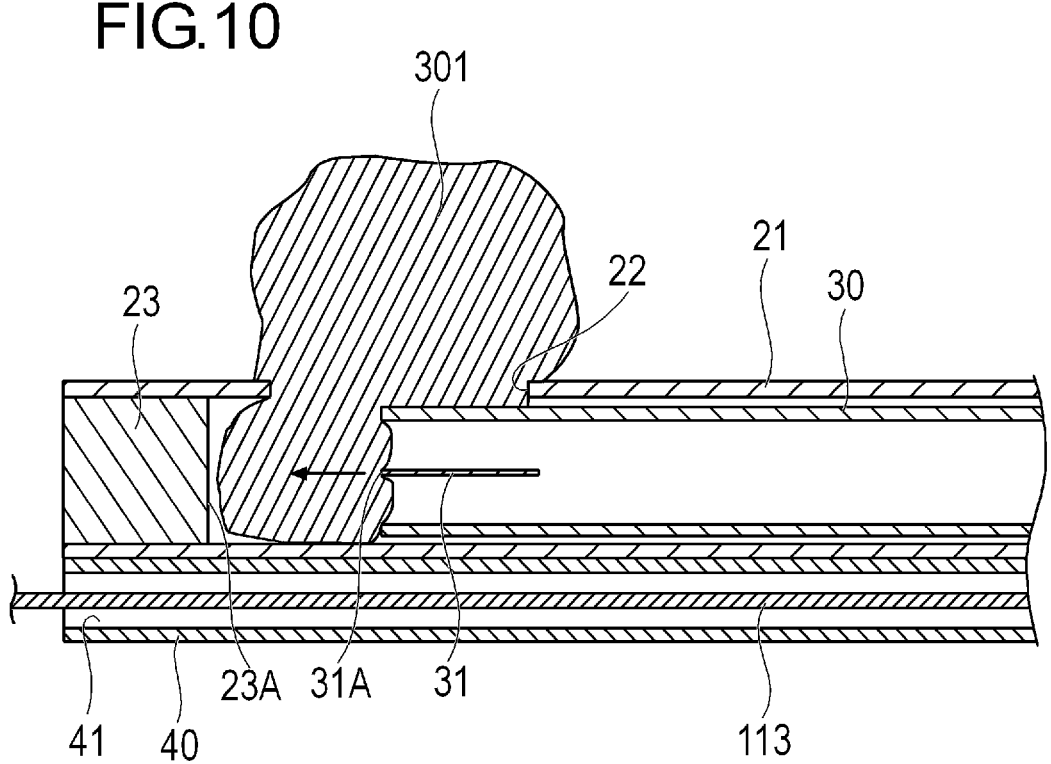
FIG. 10 is an enlarged longitudinal-sectional view of the distal portion of the medical device, which shows a process in which the thrombus aspirated to the opening portion of the shaft outer tube is severed by a shaft inner tube.

After the plunger of the syringe 100 is pulled, the shaft inner tube 30 is moved with respect to the shaft outer tube 21 in the axial direction. When the shaft inner tube 30 is moved from a state in which the shaft inner tube 30 is closer to the proximal side than the opening portion 22 to the distal side, that is, to a side so as to approach the attachment portion 23, of the shaft outer tube 21, as shown in FIG. 10, a part of the thrombus 301 infiltrating into the hollow inside of the shaft outer tube 21 from the opening portion 22 is severed while being compressed by the distal surface of the shaft inner tube 30.

Figure 11:
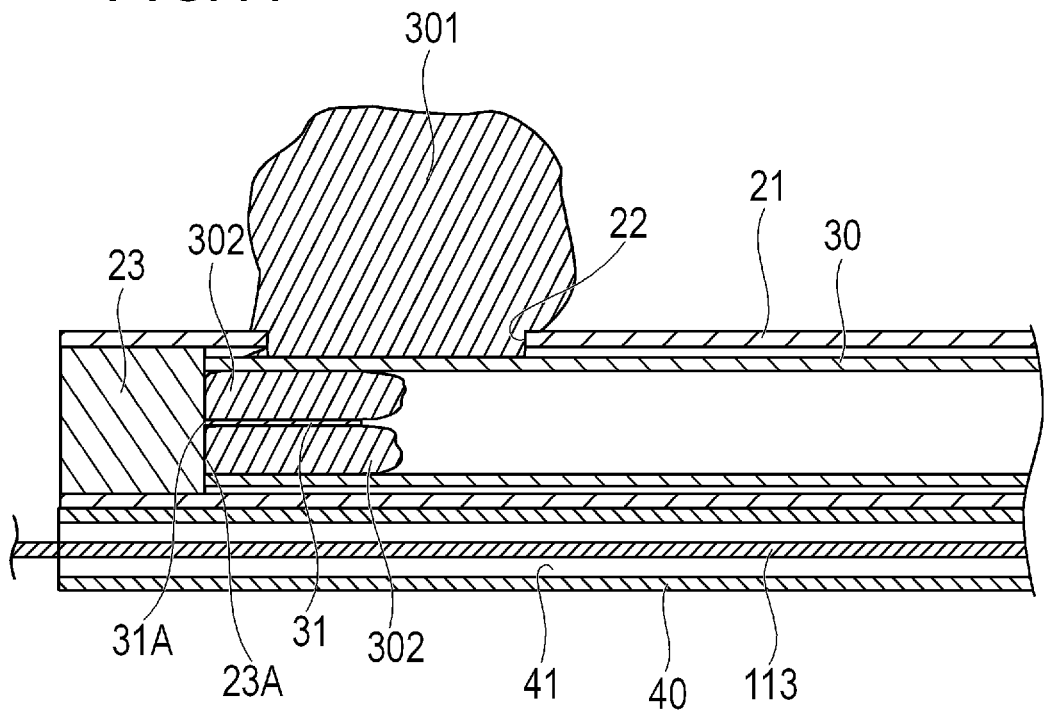
FIG. 11 is an enlarged longitudinal-sectional view of the distal portion of the medical device, which shows a state in which the thrombus severed by the shaft inner tube is cut by a cutting portion.

When the shaft inner tube 30 is moved until the distal surface of the shaft inner tube 30 is attached to the attachment surface 23A of the attachment portion 23, the severed thrombus 302 is housed in the aspiration lumen 32 of the shaft inner tube 30, as shown in FIG. 11. Here, a blade 31A of the cutting portion 31 provided in the distal portion of the shaft inner tube 30 cuts a thrombus 302 into two parts. The shaft inner tube 30 is attached to the attachment surface 23A of the attachment portion 23, and thereby the blade 31A is also attached to the attachment surface 23A, and thus the severed thrombus 302 in the hollow inside of the shaft outer tube 21 is cut by the blade 31A while the thrombus is brought into press contact with the attachment portion 23. Therefore, it is possible to reliably cut the severed thrombus 302 and thus the size of the thrombus can be smaller than an inner diameter of the shaft inner tube 30. Consequently, it is possible to suppress blocking by the severed thrombus 302 in the aspiration lumen 32 of the shaft inner tube 30.

Figure 12:
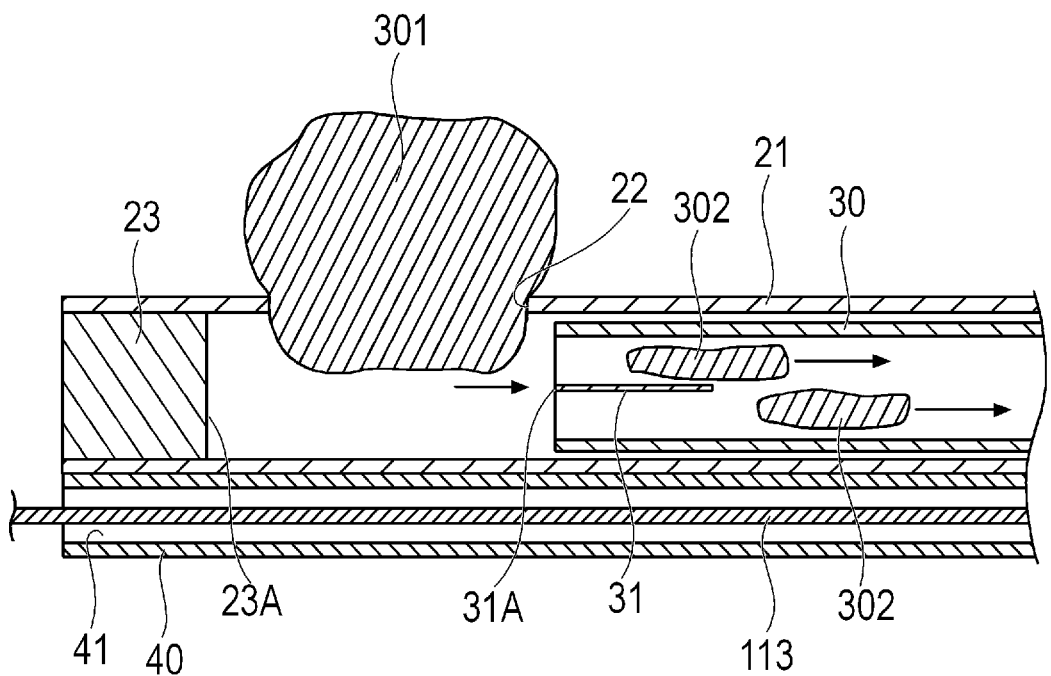
FIG. 12 is an enlarged longitudinal-sectional view of the distal portion of the medical device, which shows a process in which the thrombus cut by the cutting portion is aspirated to a proximal side of the shaft inner tube.

Since the aspiration lumen 32 of the shaft inner tube 30 is in the negative pressure state in which the syringe 100 continues to suction, as shown in FIG. 12, the severed thrombus 302 moves in the aspiration lumen 32 of the shaft inner tube 30 toward the proximal side. In addition, the shaft inner tube 30 is separated from the attachment portion 23 and is moved to the proximal side. In this manner, the opening portion 22 is reopened, and the thrombus 301 is aspirated and infiltrates into the hollow inside of the shaft outer tube 21. Hence, the shaft inner tube 30 repeats reciprocating in the axial direction, and thereby it is possible to continuously aspirate the thrombus 301 while the thrombus is finely cut.

While the crushed thrombus 301 is aspirated into the shaft portion 20, it is desirable that rotary motion of the shaft outer tube 21 is continued. The shaft outer tube 21 rotates, and thereby an eddy current of the blood occurs in the blood vessel, and the thrombus 301 is likely to be gathered in the vicinity of the rotating center, that is, in the vicinity of the center of the blood vessel in the radial direction. Therefore, the thrombus 301 is likely to be aspirated from the opening portion 22. In addition, the eddy current occurring in the vicinity of the opening portion 22 also influences flowing in the aspiration lumen 32 of the shaft inner tube 30, and swirling flow of a vortex also occurs inside the shaft inner tube 30. Consequently, it is possible to reduce flow resistance in the axial direction inside the shaft inner tube 30 and to smoothly aspirate the cut thrombus 302.

In the exemplary embodiment, the shaft outer tube 21 rotatably moves during aspiration of the thrombus 301, and the shaft inner tube 30 reciprocates with respect to the shaft outer tube 21 in the axial direction; however, a motion other than those motions may be applied thereto. For example, a motion of the shaft inner tube 30 that rotatably moves in a relatively different motion with respect to the shaft outer tube 21 (the rotating direction is a reverse direction, or the same rotating direction but different rotating speed) is applied, and thereby it is possible to more reliably sever the thrombus 301 aspirated by the opening portion 22 and to guide the thrombus to the hollow inside of the shaft outer tube 21. In addition, as the reciprocating motion is applied to the shaft outer tube 21, it is possible to crush and stir the thrombus 300 in a wider range.

After the aspiration of the thrombus 301 is completed, the reciprocating and rotational movement of the shaft outer tube 21 and the shaft inner tube 30 are stopped. Next, the crushing unit 60 is accommodated in the outer sheath 90, and the medical device 10 is removed from the blood vessel. Then, the filter device 110 is accommodated in the sheath or the like, it is removed from the blood vessel, and the treatment is completed.

As described above, according to the exemplary embodiment, the medical device 10 for crushing an object in a body lumen by being inserted into the corresponding body lumen, the device including: the elongated shaft portion 20 that is to be rotatably driven; the sliding unit 50 that is slidably interlocked with the shaft portion 20 in the axial direction of the shaft portion 20; and the crushing unit 60 that is provided with bendable wire rods, of which first end portions are fixed to the shaft portion 20 and second end portions are fixed to the sliding unit 50, and is rotatable together with the shaft portion 20. The shaft portion 20 is provided with contact portions 42 that come into contact with the sliding unit 50 during the rotation and limit relative rotation of the shaft portion 20 and the sliding unit 50. After the sliding unit 50 is attached to the contact portions 42, the sliding unit 50 rotates in the same direction as the shaft portion 20 along with the rotation of the shaft portion 20. In the medical device 10 configured as described above, the shaft portion 20 rotates, and thereby the contact portions 42 of the shaft portion 20 come into contact with the sliding unit 50 such that the relative rotation of the shaft portion 20 and the sliding unit 50 is limited. Therefore, the crushing unit 60 is unlikely to be twisted even when receiving an external force in the rotating direction and is unlikely to be deformed, and thus it is possible to appropriately maintain a range in which it is possible to crush the object by the crushing unit 60.

In a state in which the positions of the first end portion and the second end portion of the crushing unit 60 in the circumferential direction are fixed with respect to the shaft portion 20, the crushing unit 60 rotates together with the shaft portion 20. Consequently, a relative positional relationship of the first end portion and the second end portion of the crushing unit 60 does not change. Therefore, it is possible to reliably reduce twisting of the crushing unit 60 during the rotation, and it is possible to appropriately maintain the range in which it is possible to crush the object by the crushing unit 60.

In addition, the sliding unit 50 is provided with the slit 58 in the axial direction of the shaft portion 20. The shaft portion 20 is provided with the tubular body 40 (convex portion) for guide wire which is slidably fit into the slit 58. Consequently, since the tubular body 40 for guide wire can slide in the slit 58, it is possible to suppress the relative rotation of the sliding unit 50 and the shaft portion 20, while the sliding unit 50 is movable along the shaft portion 20 in the axial direction.

In addition, the shaft portion 20 has the tubular body 40 (convex portion) for guide wire. The shaft portion 20 is provided with two lumens (the lumen 24 and the guide wire lumen 41) inside, and one lumen (guide wire lumen 41) is positioned inside the tubular body 40 for guide wire. Consequently, it is possible to use the tubular body 40 for guide wire, which has the guide wire lumen 41, as a member that is fit into the slit 58, and the configuration is disposed without waste such that it is possible to reduce a diameter of the device.

In addition, the contact portions 42 are attached to the end surfaces 59 of the edges of the slit 58. Therefore, it is possible to highly efficiently transmit the rotating force from the contact portion 42 to the end surface 59.

In addition, the radius r3 of a part of the shaft portion 20 which is fit into the slit 58 is smaller than the radius r1 of the shaft portion 20 that is positioned on an inner side of the sliding unit 50. Consequently, it is possible to effectively use the part of the shaft portion 20, which has a small radius, as a convex portion that is fit into the slit 58.

In addition, the shaft portion 20 includes the shaft outer tube 21 (first tubular body) provided with the lumen 24 (first lumen) inside and the tubular body 40 (second tubular body) for guide wire which is the convex portion that is fitted into the slit 58, which is provided with the guide wire lumen 41 (second lumen) inside, and which is adjacent with the shaft outer tube 21. The radius r1 of the shaft outer tube 21 to the outer peripheral surface thereof is larger than the radius r3 of the tubular body 40 for guide wire to the outer peripheral surface thereof. Consequently, it is possible to effectively use the tubular body 40 for guide wire, which has a smaller radius than that of the shaft outer tube 21, as the convex portion that is fitted into the slit 58.

In addition, the outer diameter of the shaft outer tube 21 (first tubular body) is larger than the width between the opposite end surfaces 59 of the edges of the slit 58, and the outer diameter of the tubular body 40 (second tubular body) for guide wire is smaller than the width of the edges of the slit 58. The outer diameter of the shaft outer tube 21 is larger than the width of the slit 58, and thereby it is possible to suppress deviation of the shaft outer tube 21 from the slit 58. In addition, the outer diameter of the tubular body 40 for guide wire is smaller than the width of the slit 58, and thereby it is possible to easily move the tubular body 40 for guide wire inside the slit 58.

In addition, the disclosure also provides a treatment method for crushing the object formed in a lesion area in the body lumen by using the medical device 10 described above. The corresponding method includes a step of inserting the shaft portion 20 into the body lumen and delivering the crushing unit 60 to the lesion area and a step of rotating the crushing unit 60 by the shaft portion 20, causing the crushing unit 60 to come into contact with the object, and crushing the corresponding object. In the exemplary treatment method configured as described above, the shaft portion 20 rotates, and thereby the contact portions 42 of the shaft portion 20 come into contact with the sliding unit 50 such that the relative rotation of the shaft portion 20 and the sliding unit 50 is limited. Therefore, the crushing unit 60 is unlikely to be twisted even when receiving an external force in the rotating direction and is unlikely to be deformed, and thus it is possible to appropriately maintain the range in which it is possible to crush the object by the crushing unit 60.

Figure 13:
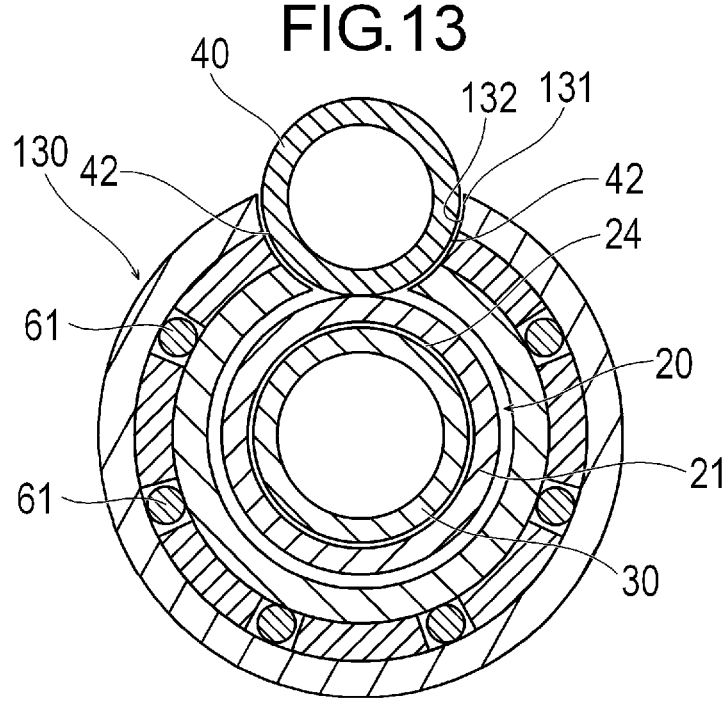
FIG. 13 is a cross-sectional view showing a first modification example of the medical device.

Note that the disclosure is not limited to only the embodiment described above, and it is possible for those skilled in the art to perform various modifications within the technical ideas of the present invention. For example, shapes of the shaft portion and the sliding unit are not limited as long as it is possible to limit the relative rotation of the shaft portion and the sliding unit during the rotation of the shaft portion. Hence, as shown in FIG. 13, end surfaces 132 of a slit 131 of a sliding unit 130 (surfaces of edge portions of the slit 131) may have a curved surface shape (surface shape) corresponding to an outer surface of the tubular body 40 for guide wire such that the end surfaces come into surface contact with the contact portions 42 of the tubular body 40 for guide wire. Consequently, the shaft portion 20 comes into contact with the sliding unit 130 on a wide area, and thus it is possible to effectively transmit a rotational driving force. Note that the same reference signs are assigned to parts having the same functions as those of the exemplary embodiment described above, and thus the description thereof is omitted.

Figure 14:
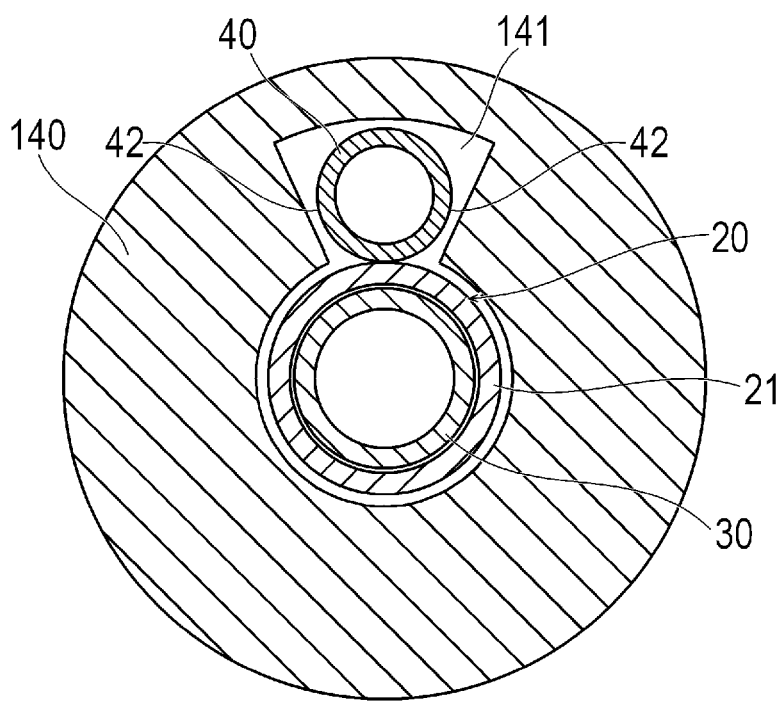
FIG. 14 is a cross-sectional view showing a second modification example of the medical device.

In addition, as shown in FIG. 14, positions of a sliding unit 140 to come into contact with the contact portions 42 of the shaft portion 20 may not be provided with the slits but may be provided with grooves 141 formed in an inner peripheral surface. Note that the same reference signs are assigned to parts having the same functions as those of the embodiment described above, and thus the description thereof is omitted.

In addition, as shown in FIG. 15(A), shapes of an outer peripheral surface of a shaft portion 150 and an inner peripheral surface of a sliding unit 160 may have an elliptic cross section that is orthogonal to the axial direction. In this manner, the outer peripheral surface of the shaft portion 150 and the inner peripheral surface of the sliding unit 160 have noncircular shapes, and thereby any part of the outer peripheral surface of the shaft portion 150 is provided with the contact portion 151 that comes into contact with the sliding unit 160 and limits relative rotation thereof. In addition, as shown in FIG. 15(B), shapes of an outer peripheral surface of a shaft portion 170 and an inner peripheral surface of a sliding unit 180 may have a quadrangular cross section that is orthogonal to the axial direction. In this manner, the outer peripheral surface of the shaft portion 170 and the inner peripheral surface of the sliding unit 180 have noncircular shapes, and thereby any part of the outer peripheral surface of the shaft portion 170 is provided with the contact portion 171 that comes into contact with the sliding unit 180 and limits relative rotation thereof. In addition, outer peripheral surfaces of the shaft portion and the sliding unit may have any shape as long as the shape is a noncircular shape on a cross-section that is orthogonal to the axial direction.

In addition, as shown in FIG. 16, an outer peripheral surface of a sliding unit 190 may be provided with a convex portion 191, and an inner peripheral surface of a shaft portion 200 may be provided with a concave portion 201 into which the convex portion 191 is fitted. When the shaft portion 200 provided with the concave portion 201 rotates, the concave portion 201 is the contact portion that comes into contact with the convex portion 191 and limits relative rotation of the sliding 190 and the shaft portion 200.

Figure 17:
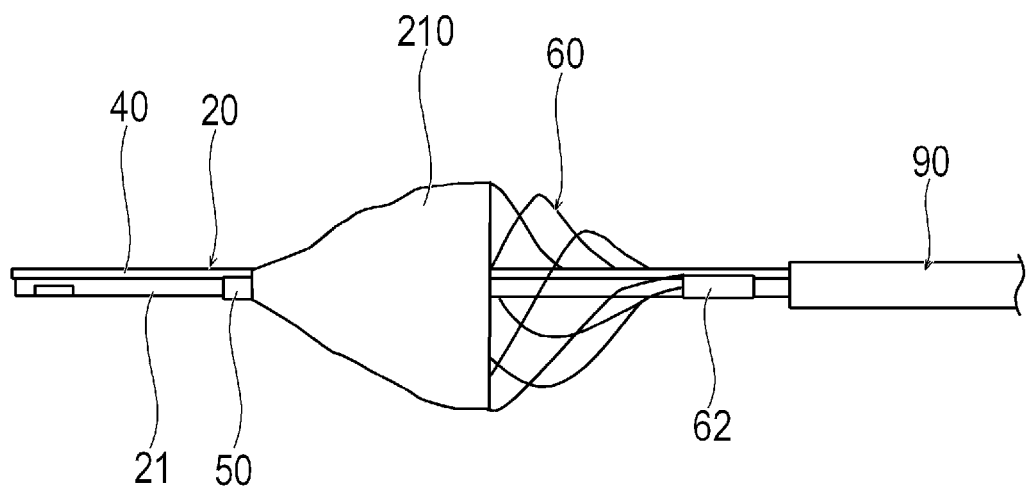
FIG. 17 is a plan view showing a sixth modification example of the medical device.

In addition, as shown in FIG. 17, the medical device may further include a film shaped cover unit 210 that is fixed to at least one part of an outer peripheral surface of the crushing unit 60. The cover unit 210 limits flow of the blood in the blood vessel. In a configuration in which the cover unit 210 is provided, the twist of the sliding unit 50 with respect to the shaft portion 20 is suppressed, and thereby it is possible to suppress a change in diameter of the cover unit 210. The change in diameter of the cover unit 210 is suppressed, and thereby it is possible to maintain a function of suppressing the flow by the cover unit 210. Note that the same reference signs are assigned to parts having the same functions as those of the embodiment described above, and thus the description thereof is omitted.

Figure 18:
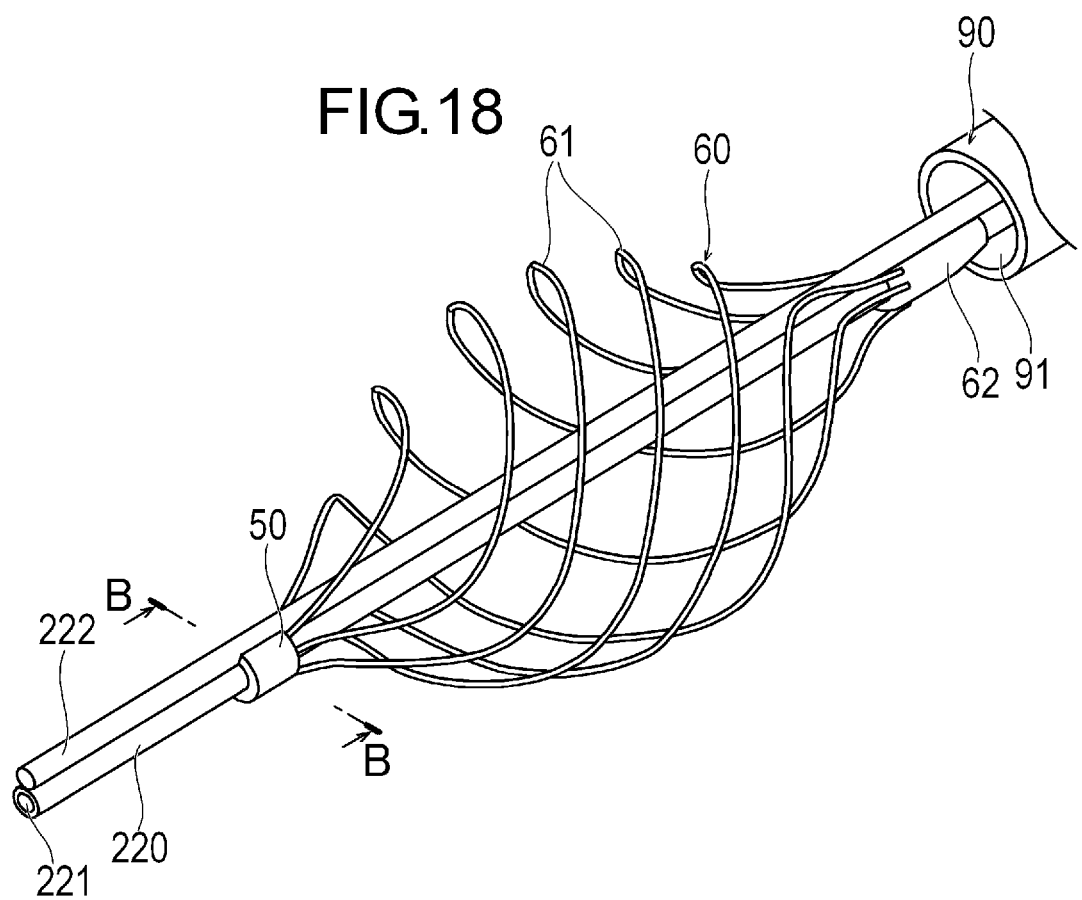
FIG. 18 is a perspective view showing a seventh modification example of the medical device.
Figure 19:
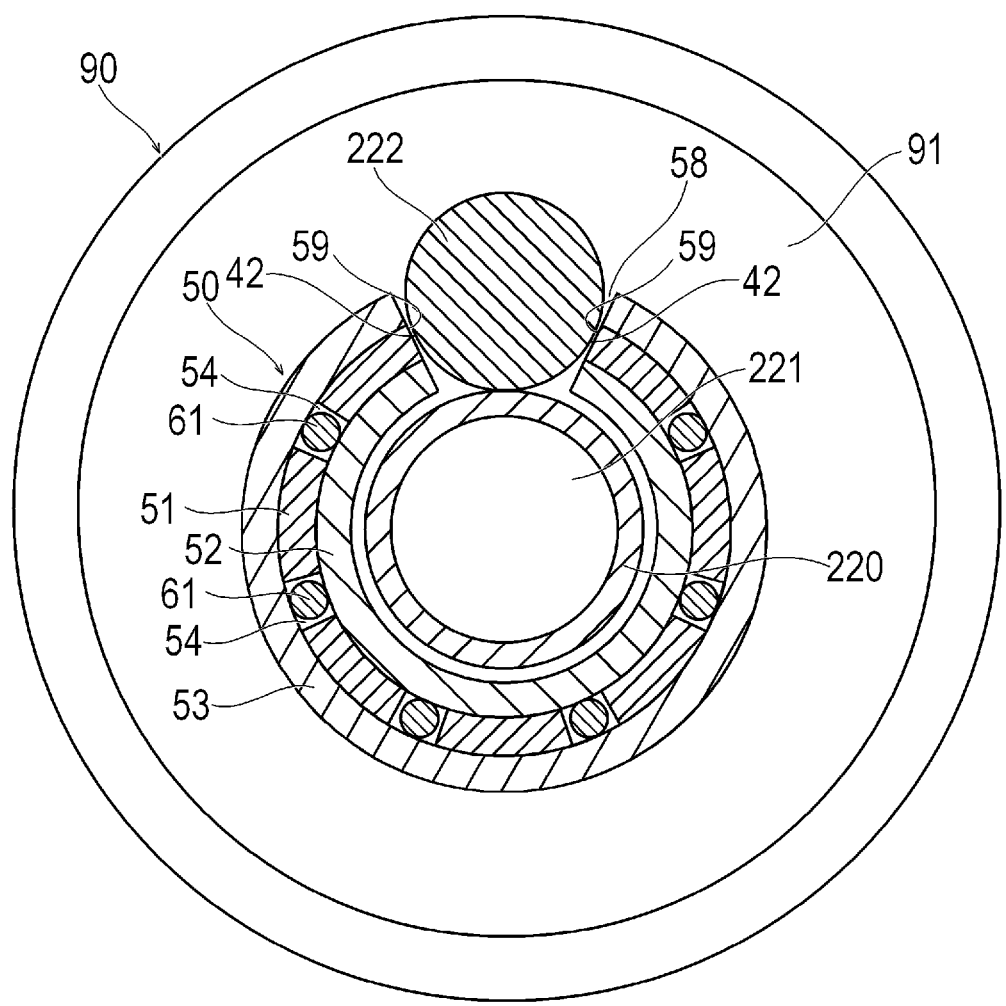
FIG. 19 is a cross-sectional view taken along line B-B in FIG. 18.

In addition, as shown in FIGS. 18 and 19, a shaft portion 220 that is positioned on an inner side of the sliding unit 50 may be provided with a guide wire lumen 221. The tubular body for guide wire may not be provided but it is possible to apply a solid member 222 as the convex portion of the slit 58, which is in contact with the end surfaces 59. The sliding unit 50 does not include an aspiration mechanism, and the thrombus 301 is aspirated by the outer sheath 90. The outer sheath 90 is able to aspirate the thrombus 301 from the opening portion on the distal side to a lumen 91 inside. It is preferable that the lumen 91 has a sufficient size so as to exhibit an aspiration force even in a state in which the shaft portion 220 and the solid member 222 are accommodated inside the lumen.

Figure 20:
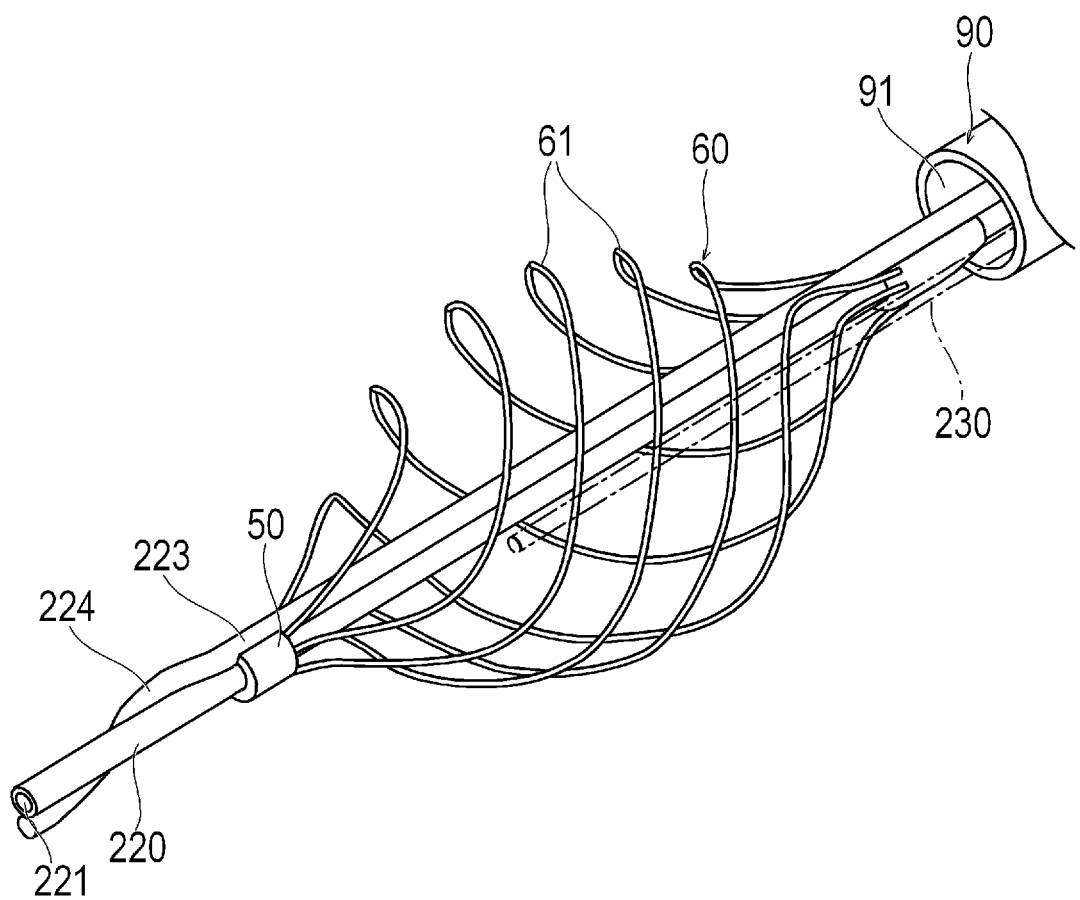
FIG. 20 is a perspective view showing an eighth modification example of the medical device.

In addition, as shown in FIG. 20, the shaft portion 220 that is positioned on the inner side of the sliding unit 50 may be provided with the guide wire lumen 221, and a solid member 223, which is the convex portion, may be provided with a spiral convex portion 224 along a circumferential surface of the shaft portion 220. The spiral convex portion 224 is able to function as a stopper that limits movement of the sliding unit 50 to a distal direction. In addition, when the sliding unit 50 moves along the spiral convex portion 224 in the axial direction, the sliding unit rotates along the spiral convex portion 224. When the sliding unit 50 rotates with respect to the shaft portion 220, the outer diameter of the crushing unit 60 changes. Therefore, the sliding unit 50 is moved along the spiral convex portion 224 in the axial direction, and thereby it is possible to further expand or retract the crushing unit 60. When the sliding unit 50 is moved along the spiral convex portion 224 in the axial direction, an elongated member 230 is inserted into the lumen 91 or the like of the outer sheath 90. The member 230 pushes the sliding unit 50, and thereby it is possible to move the sliding unit 50 along the spiral convex portion 224 in the axial direction.

Figure 21:
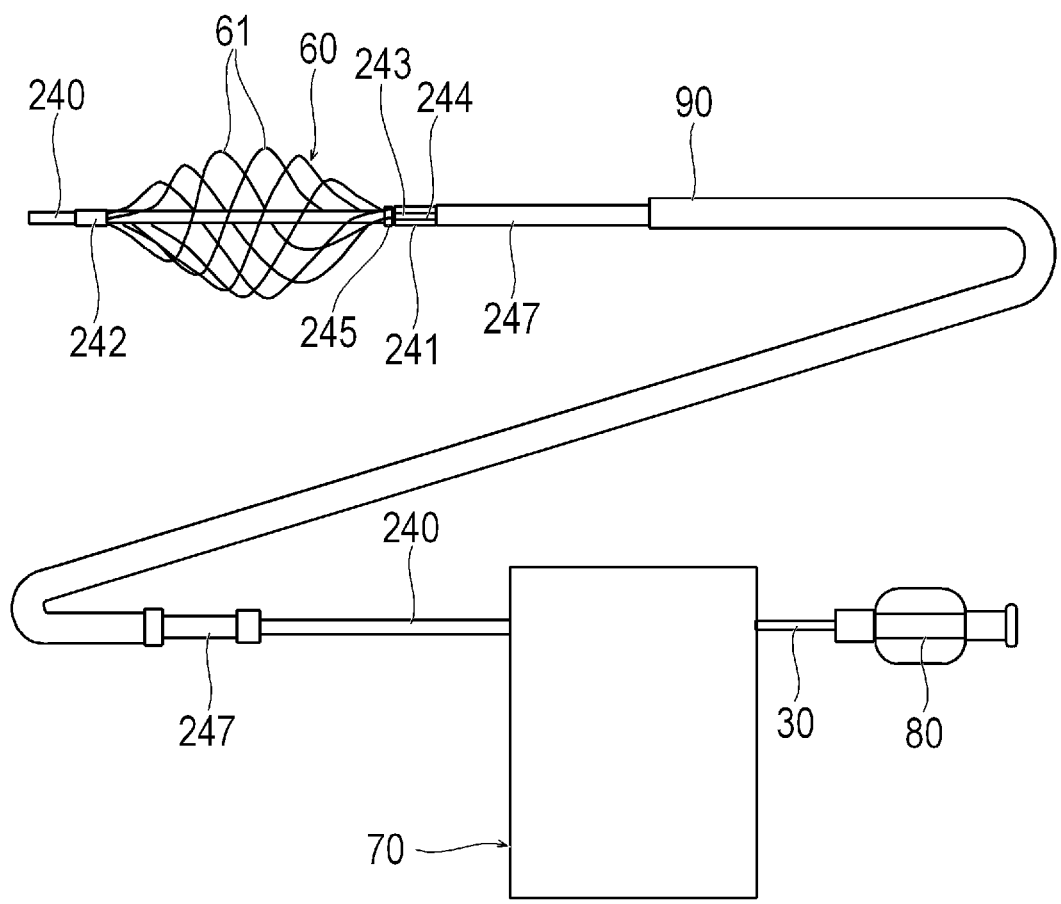
FIG. 21 is a plan view showing a ninth modification example of the medical device.
Figure 22:
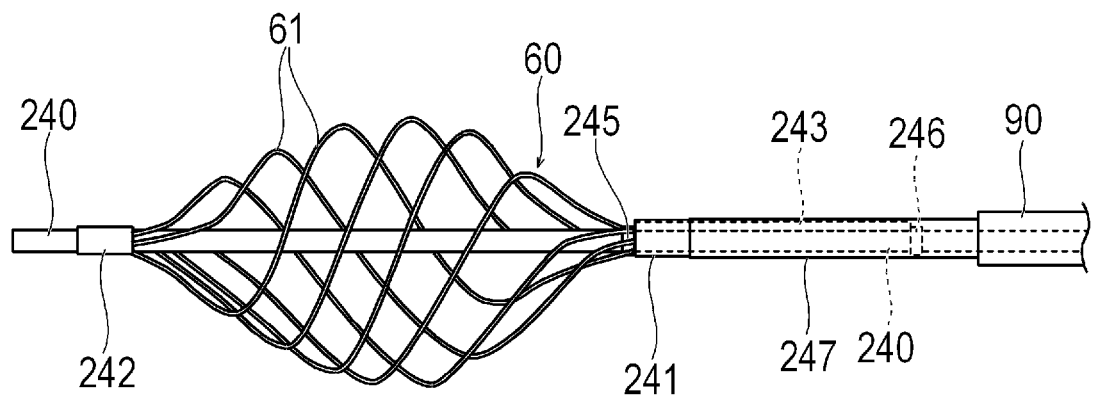
FIG. 22 is a plan view showing a distal portion in the ninth modification example.

In addition, as shown in FIGS. 21 and 22, a sliding unit 241 that is slidable with respect to a shaft portion 240 may be interlocked with the end portion of the crushing unit 60 on the proximal side thereof. Similar to the above-described exemplary embodiment, the sliding unit 241 has a C-shaped cross section that is orthogonal to the axial direction of the shaft portion 240. A guide wire lumen is provided inside the shaft portion 240. Each of the distal end portions of the crushing unit 60 is fixed to the shaft portion 240 at an interlock portion 242. Here, the interlock portion 242 may not slide with respect to the shaft portion 240. A convex portion 243 that extends in the axial direction is fixed in a range of the outer peripheral surface of the shaft portion 240, in which the sliding unit 241 is movable. The convex portion 243 is provided with a contact portion that is able to come into contact with an end surface of a slit 244 of the sliding unit 241. The convex portion 243 limits rotation of the sliding unit 241 with respect to the shaft portion 240. A distal limit portion 245 having a ring shape is fixed on the distal side of the convex portion 243 on the outer peripheral surface of the shaft portion 240. The distal limit portion 245 comes into contact with the sliding unit 241 and limits movement of the sliding unit 241 to the distal side. The movement of the sliding unit 241 to the distal side is limited, and thereby it is possible to suppress excessive expansion of the crushing unit 60. A proximal limit portion 246 having a ring shape is fixed on the proximal side of the convex portion 243 on the outer peripheral surface of the shaft portion 240. The proximal limit portion 246 comes into contact with the sliding unit 241 and limits movement of the sliding unit 241 to the proximal side. The movement of the sliding unit 241 to the proximal side is limited, and thereby it is possible to suppress damage to the crushing unit 60 due to stretching out of the crushing unit in the axial direction. The sliding unit 241 is fixed to a distal portion of an operating elongated body 247. The operating elongated body 247 movably accommodates the shaft portion 240. Hence, a part of the proximal limit portion 246 and the convex portion 243 is accommodated inside the operating elongated body 247. In addition, the operating elongated body 247 is movably accommodated in the outer sheath 90. An end portion of the operating elongated body 247 on the proximal side is positioned to be closer to the proximal side than the outer sheath 90. Hence, it is possible to operate a proximal portion of the operating elongated body 247 at hand.

A shape of the convex portion 243 is not particularly limited as long as the sliding unit 241 is slidable. Shapes of the distal limit portion 245 and the proximal limit portion 246 are not particularly limited as long as it is possible to limit the movement of the sliding unit 241.

Figure 23A:
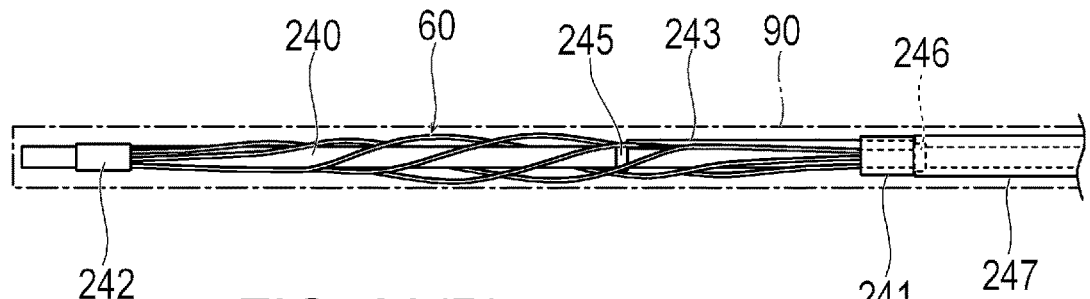
FIG. 23(A) shows a state in which the crushing unit is accommodated in an outer sheath when the crushing unit in the ninth modification example is expanded.
Figure 23B:
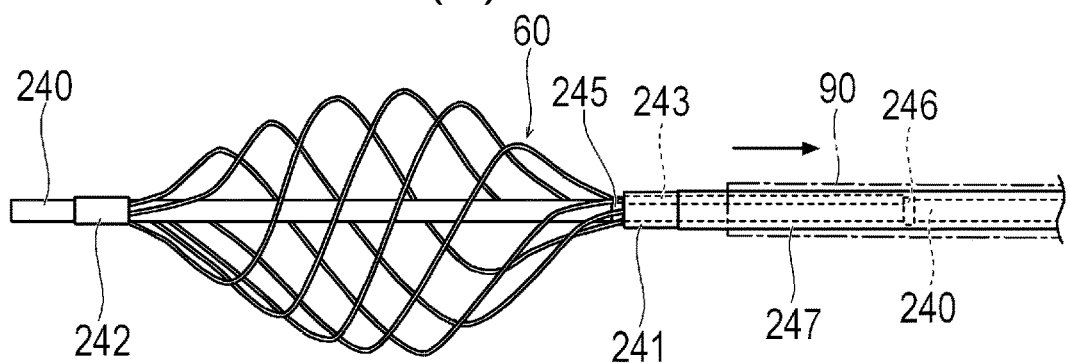
FIG. 23(B) shows a state in which the crushing unit is released from the outer sheath when the crushing unit in the ninth modification example is expanded.

In a state in which the crushing unit 60 is accommodated in the outer sheath 90, the sliding unit 241 is attached to or approaches the proximal limit portion 246 as shown in FIG. 23(A). When the crushing unit 60 accommodated in the outer sheath 90 is expanded, the outer sheath 90 is moved with respect to the shaft portion 240 to the proximal side. Consequently, as shown in FIG. 23(B), the crushing unit 60 is exposed outside the outer sheath 90 and is expanded by own elastic force. Consequently, a length of the crushing unit 60 in the axial direction is shortened. Therefore, the sliding unit 241 moves with respect to the shaft portion 240 to the distal side and is attached to or approaches the distal limit portion 245. In addition, the operating elongated body 247 also moves to the distal side along with the movement of the sliding unit 241. The relative rotation of the sliding unit 241 with respect to the shaft portion 240 is limited by the convex portion 243.

Figure 24A:
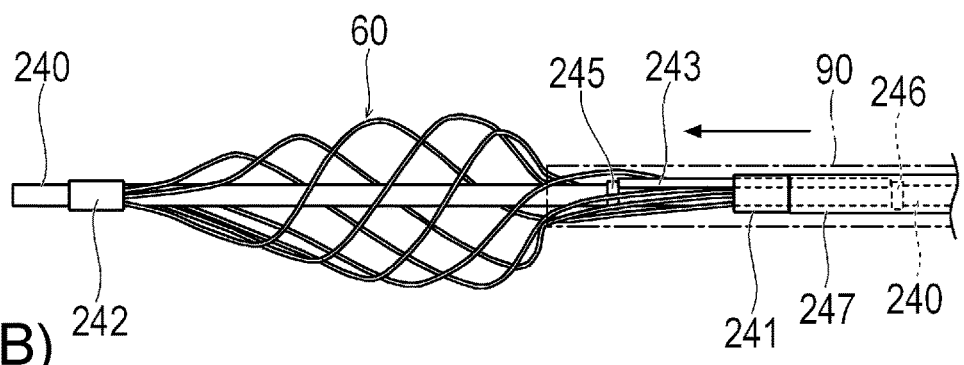
FIG. 24(A) shows a state in which the crushing unit is partially accommodated in the outer sheath when the crushing unit in the ninth modification example is retracted.
Figure 24B:
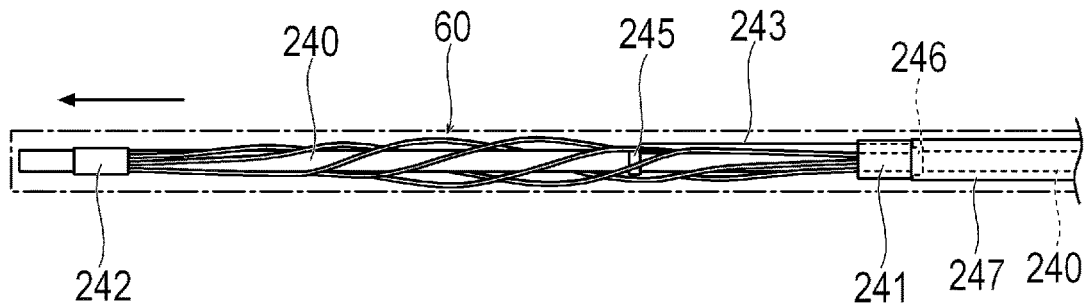
FIG. 24(B) shows a state in which the crushing unit is completely accommodated in the outer sheath when the crushing unit in the ninth modification example is retracted.

When the crushing unit 60 is accommodated in the outer sheath 90, the position of the operating elongated body 247 at hand is fixed, and the outer sheath 90 is moved toward the distal side. When a distal end portion of the outer sheath 90 comes into contact with the crushing unit 60, the crushing unit 60 is deformed in a distal direction and a retracting direction, as shown in FIG. 24(A). Hence, there is both a force for retraction in the radial direction and a force for expansion in the radial direction when the interlock portion 242 and the sliding unit 241 act on the crushing unit 60. However, the shaft portion 240 is freely movable with respect to the operating elongated body 247 and the outer sheath 90. Hence, the interlock portion 242 fixed to the shaft portion 240 can move away in the distal direction. Therefore, the force for expansion in the radial direction by pressing the crushing unit 60 in the axial direction does not significantly increase. Hence, by using the operating elongated body 247, as shown in FIG. 24(B), it is possible to accommodate the crushing unit 60 in the outer sheath 90. Therefore, it is possible to decrease the force acting on the medical device, and thus it is possible to suppress an occurrence of damage. When the crushing unit 60 is completely accommodated in the outer sheath 90, the sliding unit 241 is attached to or approaches the proximal limit portion 246.

Figure 25A:
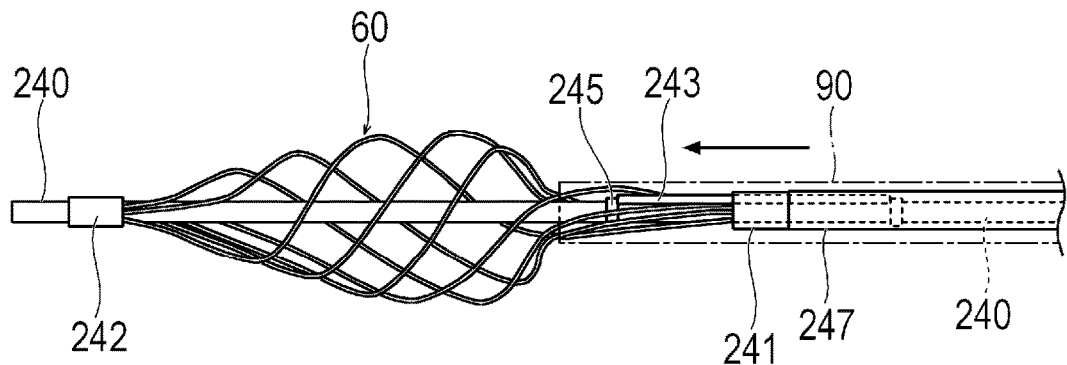
FIG. 25(A) shows a state in which the crushing unit is partially accommodated in the outer sheath when the crushing unit in the ninth modification example is retracted.
Figure 25B:
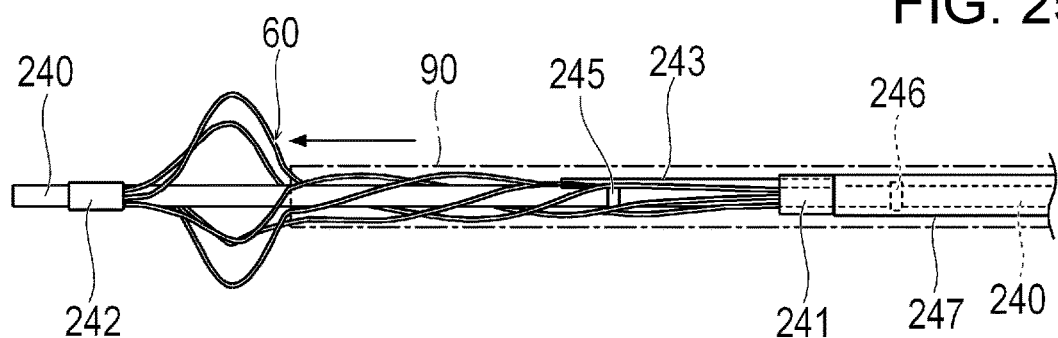
FIG. 25(B) shows a state in which the crushing unit is completely accommodated in the outer sheath when the crushing unit in the ninth modification example is retracted.

Note that, when the crushing unit 60 is accommodated in the outer sheath 90, not the position of the operating elongated body 247 but the position of the shaft portion 240 may be fixed, and the outer sheath 90 may be moved toward the distal side. In this case, the distal end portion of the outer sheath 90 comes into contact with the crushing unit 60, and the crushing unit 60 is deformed in the distal direction and the retracting direction, as shown in FIG. 25(A). Unlike the case where the operating elongated body 247 is fixed, the shaft portion 240 is fixed, and thus the interlock portion 242 is not moved. Therefore, a force for pressing between the interlock portion 242 and the sliding unit 241 strongly acts on the crushing unit 60 such that the crushing unit 60 does not move away. At an early stage of the accommodation of the crushing unit 60, a distance of a site of action (a site in which the crushing unit is in contact with the distal end portion of the outer sheath 90) on the interlock portion 242 is long, and an angle to the central axis of the crushing unit 60 in the site of contact is small. Consequently, an influence of no change of the position of the interlock portion 242 on the deformation of the crushing unit 60 is small. Therefore, the deformation of the crushing unit 60 due to the retraction in the radial direction is greater than the deformation of the crushing unit due to pressing in the axial direction. Hence, the crushing unit 60 is easily accommodated in the outer sheath 90. As shown in FIG. 25(B), at a final stage of the accommodation, a distance of the site of action on the interlock portion 242 is short, and the angle to the central axis of the crushing unit 60 in the site of contact is large.

Consequently, an influence of no change of the position of the interlock portion 242 on the deformation of the crushing unit 60 is increased. Therefore, the deformation of the crushing unit 60 due to the pressing in the axial direction is greater than the deformation of the crushing unit due to the retraction in the radial direction. Hence, in order to fix the position of the shaft portion 240 and accommodate the crushing unit 60 in the outer sheath 90, it is necessary to use a larger force, compared to a case where the position of the operating elongated body 247 is fixed. Note that, in a case where the operating elongated body 247 is not used, the operating elongated body 247 may not be provided in the medical device.

As described above, the medical device includes the operating elongated body 247 that extends along the shaft portion 240 and has a distal portion which is fixed to the sliding unit 241. Consequently, the operating elongated body 247 is operated, and thereby it is possible to control the position of the sliding unit 241. Therefore, it is possible to freely move the interlock portion 242 fixed to the sliding unit 241. Hence, when the crushing unit 60 is particularly accommodated, it is possible to smoothly accommodate the crushing unit 60 in the outer sheath 90. In addition, the force acting on the medical device decreases, and thus it is possible to suppress damage to the medical device.

Figure 26:
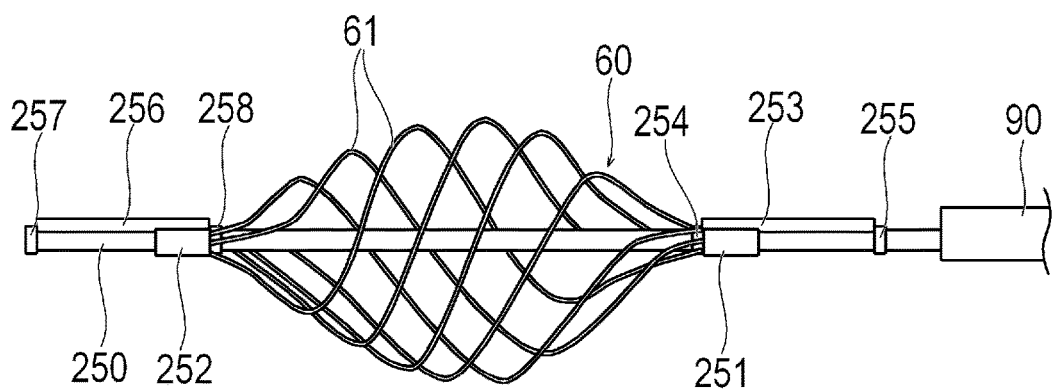
FIG. 26 is a plan view showing a tenth modification example of the medical device.

In addition, as shown in FIG. 26, the medical device may include a first sliding unit 251 and a second sliding unit 252 that are slidable along a shaft portion 250. Similar to the above-described embodiment, the sliding unit 251 on the proximal side and the sliding unit 252 on the distal side have a C-shaped cross section that is orthogonal to the axial direction of the shaft portion 250. The end portion of the crushing unit 60 on the proximal side is fixed to the proximal sliding unit 251. The end portion of the crushing unit 60 on the distal side is fixed to the distal sliding unit 252.

A proximal convex portion 253 that extends in the axial direction is fixed in a range of the outer peripheral surface of the shaft portion 250, in which the proximal sliding unit 251 is movable. The proximal convex portion 253 is provided with a contact portion that is able to come into contact with an end surface of a slit of the proximal sliding unit 251. The proximal convex portion 253 limits rotation of the proximal sliding unit 251 with respect to the shaft portion 250. A first distal limit portion 254 having a ring shape is fixed on the distal side of the proximal convex portion 253 on the outer peripheral surface of the shaft portion 250. The first distal limit portion 254 limits movement of the proximal sliding unit 251 to the distal side. The movement of the proximal sliding unit 251 to the distal side is limited, and thereby it is possible to suppress excessive expansion of the crushing unit 60. A first proximal limit portion 255 having a ring shape is fixed on the proximal side of the proximal convex portion 253 on the outer peripheral surface of the shaft portion 250. The first proximal limit portion 255 limits movement of the proximal sliding unit 251 to the proximal side. The movement of the proximal sliding unit 251 to the proximal side is limited, and thereby it is possible to suppress damage to the crushing unit 60 due to stretching out of the crushing unit in the axial direction.

A distal convex portion 256 that extends in the axial direction is fixed in a range of the outer peripheral surface of the shaft portion 250, in which the distal sliding unit 252 is movable. The distal convex portion 256 is provided with a contact portion that is able to come into contact with an end surface of a slit of the distal sliding unit 252. The distal convex portion 256 limits rotation of the distal sliding unit 252 with respect to the shaft portion 250. A second distal limit portion 257 having a ring shape is fixed on the distal side of the distal convex portion 256 on the outer peripheral surface of the shaft portion 250. The second distal limit portion 257 limits movement of the distal sliding unit 252 to the distal side. The movement of the distal sliding unit 252 to the distal side is limited, and thereby it is possible to suppress excessive expansion of the crushing unit 60. A second proximal limit portion 258 having a ring shape is fixed on the proximal side of the distal convex portion 256 on the outer peripheral surface of the shaft portion 250. The second proximal limit portion 258 limits movement of the distal sliding unit 252 to the proximal side. The movement of the distal sliding unit 252 to the proximal side is limited, and thereby it is possible to suppress damage to the crushing unit 60 due to stretching out of the crushing unit in the axial direction.

The proximal convex portion 253 and the distal convex portion 256 are different convex portions and are separated from each other in the axial direction. The proximal convex portion 253 and the distal convex portion 256 may be positioned to be coaxial or not to be coaxial with each other. Note that shapes of the proximal convex portion 253 and the distal convex portion 256 are not particularly limited as long as the proximal sliding unit 251 and the distal sliding unit 252 are slidable. Shapes of the first proximal limit portion 255 and the first distal limit portion 254 are not particularly limited as long as it is possible to limit the movement of the proximal sliding unit 251. In addition, shapes of the second distal limit portion 257 and the second proximal limit portion 258 are not particularly limited as long as it is possible to limit the movement of the distal sliding unit 252.

Figure 27A:
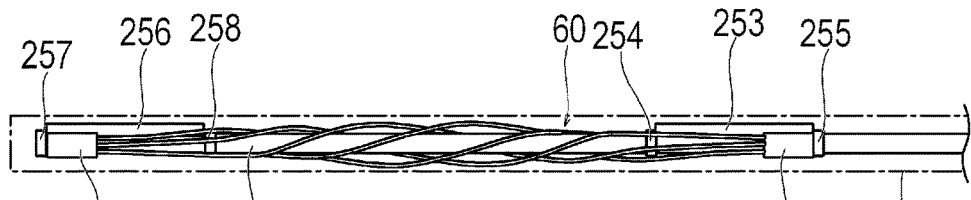
FIG. 27(A) shows a state in which the crushing unit is accommodated in an outer sheath when the crushing unit in the tenth modification example is expanded.
Figure 27B:
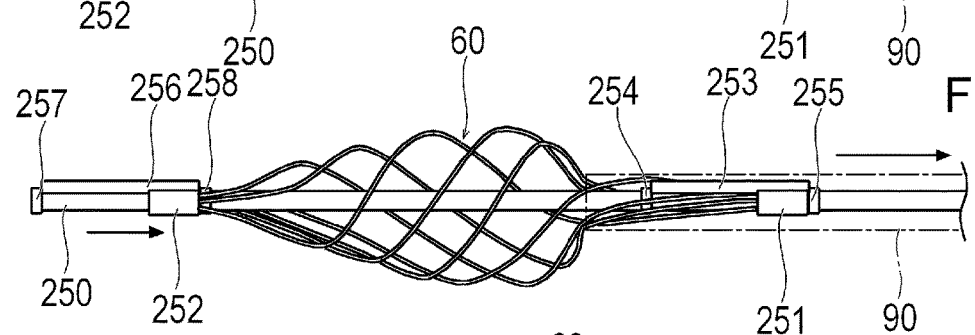
FIG. 27(B) shows a state in which the crushing unit is partially released from the outer sheath when the crushing unit in the tenth modification example is expanded.
Figure 27C:
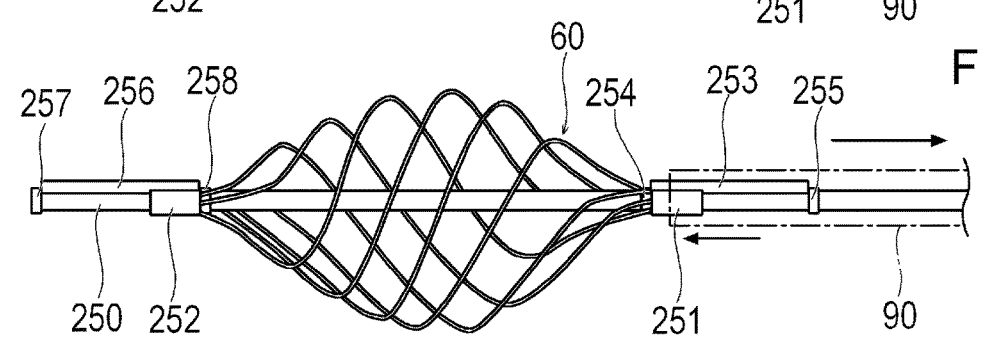
FIG. 27(C) shows a state in which the crushing unit is completely released from the outer sheath when the crushing unit in the tenth modification example is expanded.

In a state in which the crushing unit 60 is accommodated in the outer sheath 90, the proximal sliding unit 251 is attached to or approaches the first proximal limit portion 255 as shown in FIG. 27(A). In addition, the distal sliding unit 252 is attached to or approaches the second distal limit portion 257. When the crushing unit 60 accommodated in the outer sheath 90 is expanded, the outer sheath 90 is moved with respect to the shaft portion 250 to the proximal side. Consequently, as shown in FIG. 27(B), the proximal sliding unit 251 is attached to the first proximal limit portion 255, and the crushing unit 60 is gradually exposed from the outer sheath 90 and is expanded by its own elastic force. Consequently, a length of the crushing unit 60 in the axial direction is shortened. Therefore, the distal sliding unit 252 moves to the proximal side and is attached to the second proximal limit portion 258. When the outer sheath 90 is further moved with respect to the shaft portion 250 to the proximal side, the crushing unit 60 is exposed from the outer sheath 90 and is expanded by its own elastic force, as shown in FIG. 27(C). Consequently, the length of the crushing unit 60 in the axial direction is shortened, the proximal sliding unit 251 moves to the distal side and is attached to the first distal limit portion 254. Consequently, the crushing unit 60 is completely expanded. The relative rotation of the proximal sliding unit 251 and the distal sliding unit 252 with respect to the shaft portion 250 is limited by the proximal convex portion 253 and the distal convex portion 256.

Figure 28A:
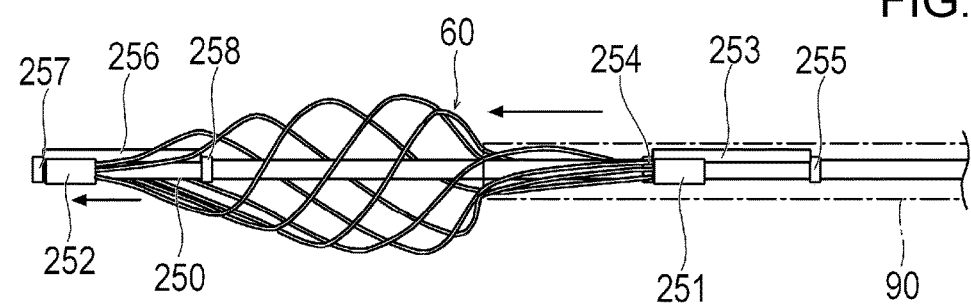
FIG. 28(A) shows a state in which the crushing unit is partially accommodated in the outer sheath when the crushing unit in the tenth modification example is retracted.
Figure 28B:
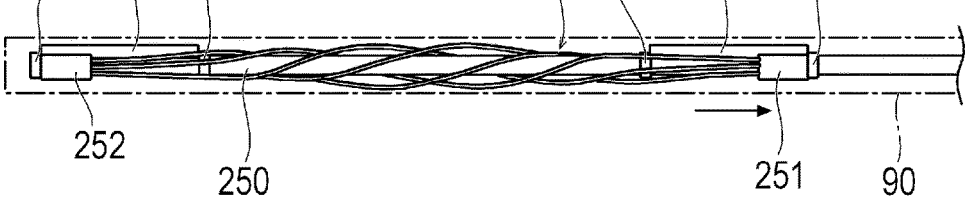
FIG. 28(B) shows a state in which the crushing unit is completely accommodated in the outer sheath when the crushing unit in the tenth modification example is retracted.

When the crushing unit 60 is accommodated in the outer sheath 90, the shaft portion 250 is fixed at hand, and the outer sheath 90 is moved toward the distal side. When the distal end portion of the outer sheath 90 comes into contact with the crushing unit 60, the crushing unit 60 is deformed in the distal direction and the retracting direction, as shown in FIG. 28(A). Consequently, a length of the crushing unit 60 in the axial direction is elongated. Therefore, the distal sliding unit 252 is moved to the distal side and is attached to the second distal limit portion 257. When the distal sliding unit 252 is attached to the second distal limit portion 257, it is not possible for the distal sliding unit 252 to move with respect to the shaft portion 250. Therefore, a force for pressing between the distal sliding unit 252 and the proximal sliding unit 251 in the axial direction acts on the crushing unit 60. Consequently, as shown in FIG. 28(B), the crushing unit 60 is completely accommodated in the outer sheath 90 while being retracted in the radial direction, and the length of crushing unit in the axial direction increases. Hence, the proximal sliding unit 251 moves to the proximal side and is attached to or approaches the first proximal limit portion 255.

As described above, in the medical device, the contact portions of the proximal convex portion 253 and the distal convex portion 256, which come into contact with the proximal sliding unit 251 and the distal sliding unit 252, respectively, are divided in the axial direction. Consequently, a moving distance of the proximal sliding unit 251 and the distal sliding unit 252, which move in the axial direction such that the crushing unit 60 is expanded, can be distributed into two distances. Therefore, since not one long contact portion but two short contact portions are provided, flexibility of the shaft portion 250 is improved, and the operability in the living body is improved.

In addition, the medical device includes the first distal limit portion 254 and the second distal limit portion 257, which limit movement of the proximal sliding unit 251 and the distal sliding unit 252 to the distal side with respect to the shaft portion 250, and the first proximal limit portion 255 and the second proximal limit portion 258, which limit the movement thereof to the proximal side. Consequently, the movement of the crushing unit 60 is limited such that the crushing unit 60 can be released from the outer sheath 90 and accommodated in the outer sheath 90. In addition, since the size of the crushing unit 60 is appropriately maintained, it is possible to reduce a burden on the living body, and it is possible to suppress the damage to the medical device. Note that, in the modification example, the two distal limit portions (the first distal limit portion 254 and the second distal limit portion 257), which limit the movement of the sliding units (the sliding unit 251 and the distal sliding unit 252) with respect to the shaft portion 250 to the distal side are provided; however, only one of the distal limit portions may be provided. In addition, in the modification example, the two proximal limit portions (the first proximal limit portion 255 and the second proximal limit portion 258), which limit the movement of the sliding units (the sliding unit 251 and the distal sliding unit 252) to the proximal side with respect to the shaft portion 250 are provided; however, only one of the proximal limit portions may be provided.

In addition, the body lumen, into which the medical device 10 is inserted, is not limited to the blood vessel, and examples thereof may include a vessel, a ureter, a bile duct, an oviduct, a hepatic duct, or the like.

In addition, the medical device may not have an aspirating function. In addition, the sliding unit may not be connected to the end portion of the crushing unit on the distal side thereof but may be interlocked with the end portion thereof on the proximal side. In addition, the shaft portion may be provided with three or more lumens or may be provided with only one lumen. In addition, the sliding unit may not need to be configured of three members (the central sliding portion 51, the inner sliding portion 52, and the outer sliding portion 53).

The detailed description above describes features, characteristics and operational aspects of embodiments of a medical device and treatment method representing examples of the same disclosed herein. The disclosure and the present invention are not limited, however, to the precise embodiments and variations described. Various changes, modifications and equivalents could be effected by one skilled in the art without departing from the spirit and scope of the disclosure as defined in the appended claims. It is expressly intended that all such changes, modifications and equivalents which fall within the scope of the claims are embraced by the claims.

What is claimed is:

1. A medical device for crushing an object in a body lumen when inserted into the corresponding body lumen, the device comprising:
    an elongated shaft portion;
    a crushing unit located on the shaft portion and provided with a plurality of bendable wire rods; and
    a sliding unit fixed to end portions of the wire rods on at least one of a distal side or a proximal side thereof, the sliding unit being slidable in an axial direction of the shaft portion,
    wherein the sliding unit comprises a central sliding portion and an inner sliding portion provided radially inward of the central sliding portion, the central sliding portion including a first slit and a plurality of concave portions, the end portions of the wire rods being accommodated in the plurality of concave portions, the inner sliding portion including a second slit, and the first and second slits being aligned with one another to define a slit in an axial direction of the sliding unit.

2. The medical device according to claim 1, wherein an outer peripheral surface of the shaft portion and an inner peripheral surface of the sliding unit have a noncircular shape.

3. The medical device according to claim 1, further comprising a cover unit fixed to at least one part of an outer peripheral surface of the crushing unit.

4. The medical device according to claim 1, wherein the shaft portion includes a plurality of tubular bodies, and at least one of said plurality of tubular bodies is accommodated in the slit.

5. The medical device according to claim 1, wherein the central sliding portion is fixed to the inner sliding portion by an adhesive.

6. A medical device for crushing an object in a body lumen when inserted into the corresponding body lumen, the device comprising:
    an elongated shaft portion;
    a crushing unit located on the shaft portion and provided with a plurality of bendable wire rods; and
    a sliding unit fixed to an end portion of the wire rods on at least one of a distal side or a proximal side thereof, the sliding unit being slidable in an axial direction of the shaft portion,
    wherein the sliding unit comprises a central sliding portion and an outer sliding portion provided radially outward of the central sliding portion, the central sliding portion including a first slit and a plurality of concave portions, the end portions of the wire rods being accommodated in the plurality of concave portions, the outer sliding portion including a second slit, and the first and second slits being aligned with one another to define a slit in an axial direction of the sliding unit.

7. The medical device according to claim 6, wherein an outer peripheral surface of the shaft portion and an inner peripheral surface of the sliding unit have a noncircular shape.

8. The medical device according to claim 6, further comprising a cover unit fixed to at least one part of an outer peripheral surface of the crushing unit.

9. The medical device according to claim 6, wherein the shaft portion includes a plurality of tubular bodies, and at least one of said plurality of tubular bodies is accommodated in the slit.

10. The medical device according to claim 6, wherein the central sliding portion is fixed to the outer sliding portion by an adhesive.

11. A medical device for crushing an object in a body lumen when inserted into the corresponding body lumen, the device comprising:
   an elongated shaft portion;
   a crushing unit located on the shaft portion and provided with a plurality of bendable wire rods; and
   a sliding unit fixed to an end portion of the wire rods on at least one of a distal side or a proximal side thereof, the sliding unit being slidable in an axial direction of the shaft portion,
   wherein the sliding unit comprises a central sliding portion, an inner sliding portion provided radially inward of the central sliding portion, and an outer sliding portion provided radially outward of the central sliding portion, the central sliding portion including a first slit and a plurality of concave portions, the end portions of the wire rods being accommodated in the plurality of concave portions, the inner sliding portion including a second slit, the outer sliding portion including a third slit, and the first, second and third slits being aligned with one another to define a slit in an axial direction of the sliding unit.

12. The medical device according to claim 11, wherein an outer peripheral surface of the shaft portion and an inner peripheral surface of the sliding unit have a noncircular shape.

13. The medical device according to claim 11, further comprising a cover unit fixed to at least one part of an outer peripheral surface of the crushing unit.

14. The medical device according to claim 11, wherein the shaft portion includes a plurality of tubular bodies, and at least one of said plurality of tubular bodies is accommodated in the slit.

15. The medical device according to claim 11, wherein the central sliding portion is fixed to the inner sliding portion and the outer sliding portion by an adhesive.

* * * * *